(12) United States Patent (10) Patent No.: US 9,452,249 B2
Kearsley et al. (45) Date of Patent: Sep. 27, 2016

(54) MODULAR DRIVELINE

(71) Applicant: Thoratec Corporation, Pleasanton, CA (US)

(72) Inventors: Keith H. Kearsley, Burlington, MA (US); Christopher J. Cotter, Newburyport, MA (US); Justin A. Callaway, Goffstown, NH (US); Maria D. Kulinski, Middleton, MA (US); John C. Layton, Dublin, CA (US); Ramesh B. Jayaraman, Fremont, CA (US)

(73) Assignee: THORATEC CORPORATION, Pleasanton, CA (US)

( * ) Notice: Subject to any disclaimer, the term of this patent is extended or adjusted under 35 U.S.C. 154(b) by 132 days.

(21) Appl. No.: 14/316,277

(22) Filed: Sep. 9, 2014

(65) Prior Publication Data

US 2015/0031937 A1 Jan. 29, 2015

Related U.S. Application Data

(63) Continuation of application No. 13/314,806, filed on Dec. 8, 2011, now Pat. No. 8,794,989.

(60) Provisional application No. 61/420,908, filed on Dec. 8, 2010.

(51) Int. Cl.
*H01R 4/24* (2006.01)
*A61M 1/10* (2006.01)
(Continued)

(52) U.S. Cl.
CPC .......... *A61M 1/1008* (2014.02); *A61M 1/1086* (2013.01); *A61M 1/122* (2014.02);
(Continued)

(58) Field of Classification Search
CPC .......... A61M 1/1008; A61M 1/1086; A61M 1/122; A61M 1/127; A61M 2205/04; H01B 7/048; H01R 13/622; H01R 2201/12; H01R 13/685
USPC ........................................................ 439/339
See application file for complete search history.

(56) References Cited

U.S. PATENT DOCUMENTS 4,193,657 A 3/1980 Slone et al.
4,688,998 A 8/1987 Olsen et al.
(Continued)

FOREIGN PATENT DOCUMENTS

CN 300837668 10/2008
EP 790624 8/1997
(Continued)

OTHER PUBLICATIONS

Barletta et al., "Design of a bearing less blood pump", Proc.3rd Int. Symp. on Magnetic Suspension Technology, Dec. 13-15, 1995, pp. 265-274.

*Primary Examiner* — Jean F Duverne
(74) *Attorney, Agent, or Firm* — Kilpatrick Townsend & Stockton LLP

(57) ABSTRACT

A modular driveline includes a modular portion including a cable and a connector, the cable having terminations, and a percutaneous portion including a cable and a connector, the cable having terminations. The percutaneous portion connector couples to the modular portion connector, and cable terminations at the connectors are captured in the connectors by potting. The cable can include an inner member, conductors disposed about the inner member, a covering about the conductors, a layer extruded onto the covering, an armor braid over the extruded layer, and an outer jacket extruded over the armor braid.

35 Claims, 20 Drawing Sheets

(51) Int. Cl.
*A61M 1/12* (2006.01)
*H01B 7/04* (2006.01)
*H01R 13/622* (2006.01)

(52) U.S. Cl.
CPC ............. *A61M 1/127* (2013.01); *H01B 7/048* (2013.01); *H01R 13/622* (2013.01); *A61M 2205/04* (2013.01); *H01R 2201/12* (2013.01)

(56) References Cited

U.S. PATENT DOCUMENTS

| | | | |
|---|---|---|---|
| 4,895,557 A * | 1/1990 | Moise | A61M 1/101 |
| | | | 415/900 |
| 5,055,005 A | 10/1991 | Kletschka | |
| 5,195,877 A | 3/1993 | Kletschka | |
| 5,470,208 A | 11/1995 | Kletschka | |
| 5,571,028 A | 11/1996 | Szegda et al. | |
| 5,708,346 A | 1/1998 | Schoeb | |
| 6,011,993 A | 1/2000 | Tziviskos et al. | |
| 6,305,962 B1 * | 10/2001 | Maher | H01R 13/585 |
| | | | 439/27 |
| 7,150,567 B1 | 12/2006 | Luther et al. | |
| 7,182,727 B2 | 2/2007 | Aboul-Hosn et al. | |
| 7,229,258 B2 | 6/2007 | Wood et al. | |
| 7,264,606 B2 | 9/2007 | Jarvik et al. | |
| 7,462,019 B1 | 12/2008 | Allarie et al. | |
| 7,541,543 B2 | 6/2009 | Head et al. | |
| 7,806,714 B2 | 10/2010 | Williams et al. | |
| 7,824,204 B2 | 11/2010 | Fujiwara et al. | |
| 8,241,309 B2 | 8/2012 | Miles et al. | |
| 8,366,599 B2 | 2/2013 | Tansley et al. | |
| 8,382,830 B2 | 2/2013 | Maher et al. | |
| 2005/0071001 A1 * | 3/2005 | Jarvik | A61M 1/122 |
| | | | 623/3.28 |
| 2006/0074271 A1 | 4/2006 | Cotter | |
| 2007/0213690 A1 | 9/2007 | Phillips et al. | |
| 2008/0306327 A1 * | 12/2008 | Shifflette | A61M 1/101 |
| | | | 600/16 |
| 2010/0256440 A1 | 10/2010 | Maher et al. | |
| 2011/0072658 A1 | 3/2011 | Dye et al. | |
| 2011/0160516 A1 | 6/2011 | Dague et al. | |
| 2011/0218383 A1 * | 9/2011 | Broen | A61M 1/127 |
| | | | 600/16 |
| 2011/0298304 A1 * | 12/2011 | Cotter | A61M 1/127 |
| | | | 307/147 |
| 2012/0010709 A1 | 1/2012 | Wilson et al. | |
| 2012/0130153 A1 * | 5/2012 | Bolyard | A61M 1/1086 |
| | | | 600/17 |
| 2012/0289881 A1 * | 11/2012 | Lyu | A61M 1/1678 |
| | | | 604/9 |

FOREIGN PATENT DOCUMENTS

| | | |
|---|---|---|
| EP | 806779 | 11/1997 |
| EP | 1863040 | 12/2007 |
| WO | 0191851 | 12/2001 |
| WO | 03011138 | 2/2003 |
| WO | 2008154393 | 12/2008 |
| WO | 2010025411 | 3/2010 |

* cited by examiner

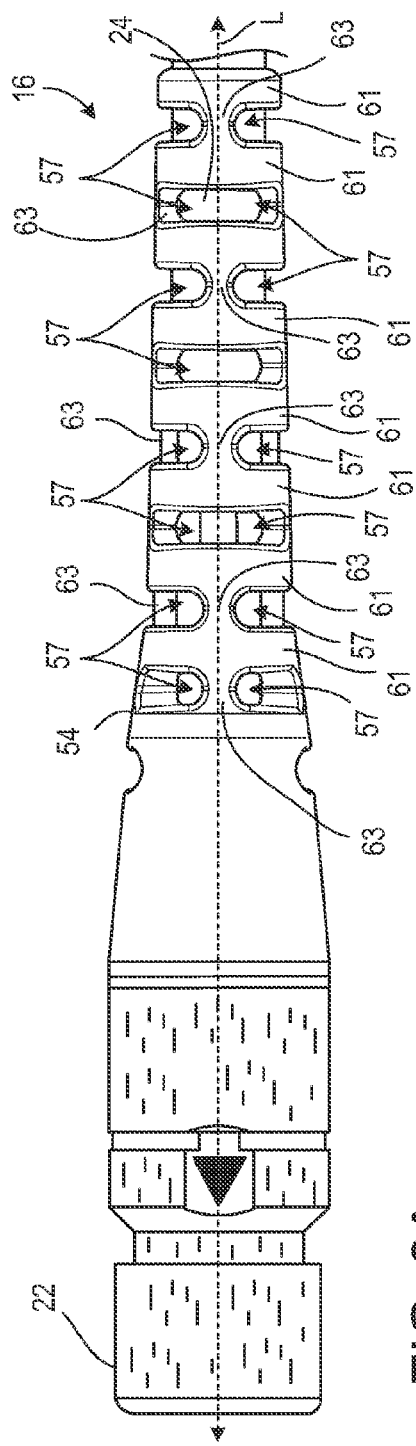
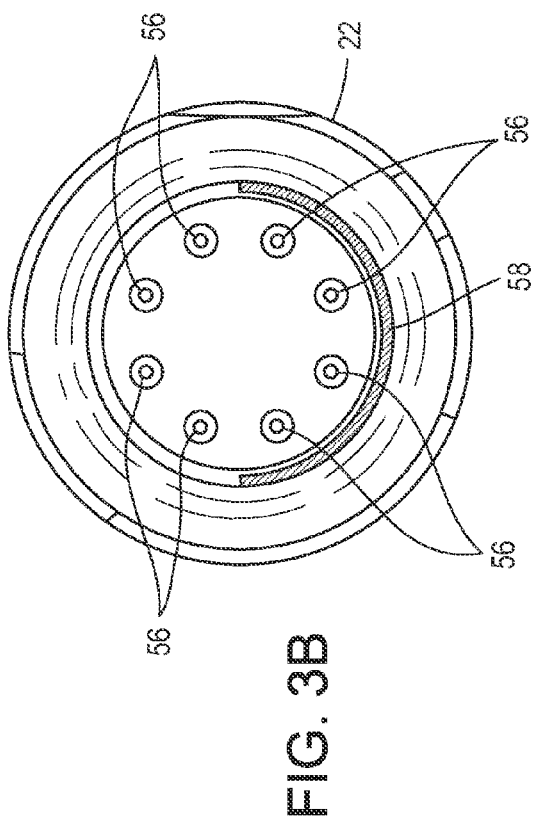
FIG. 3A
FIG. 3B

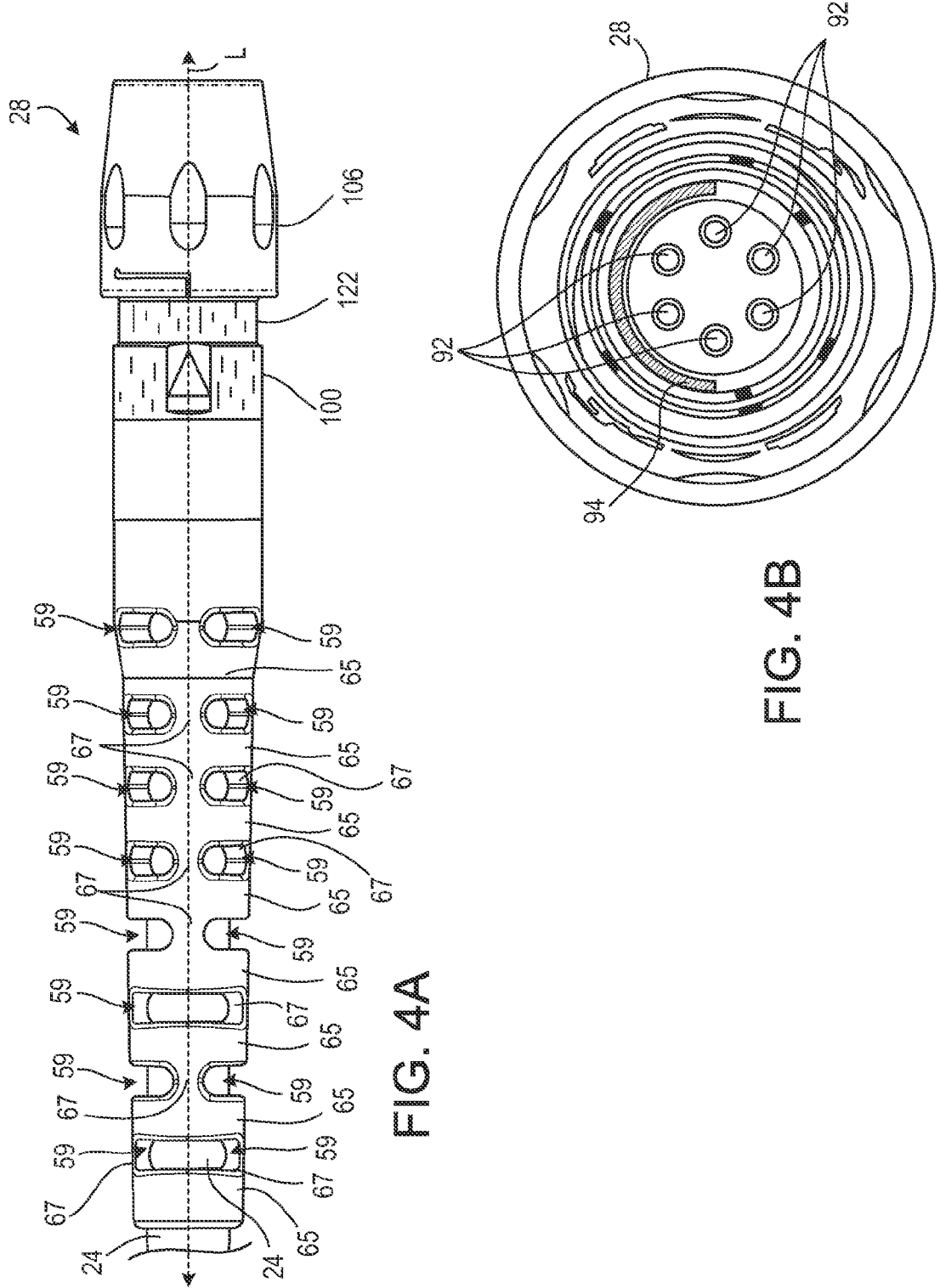

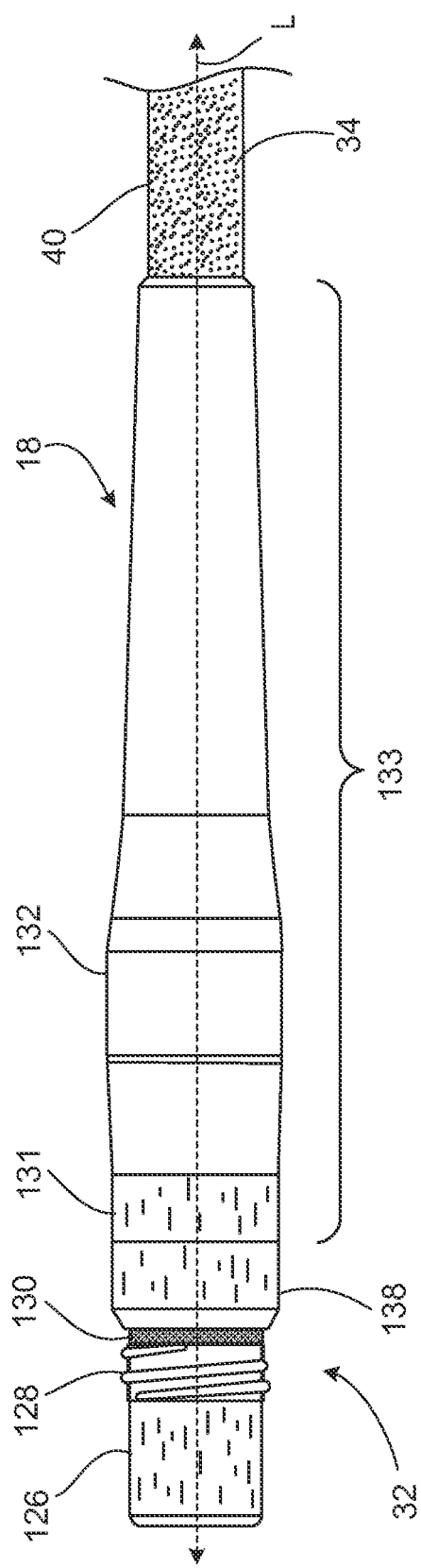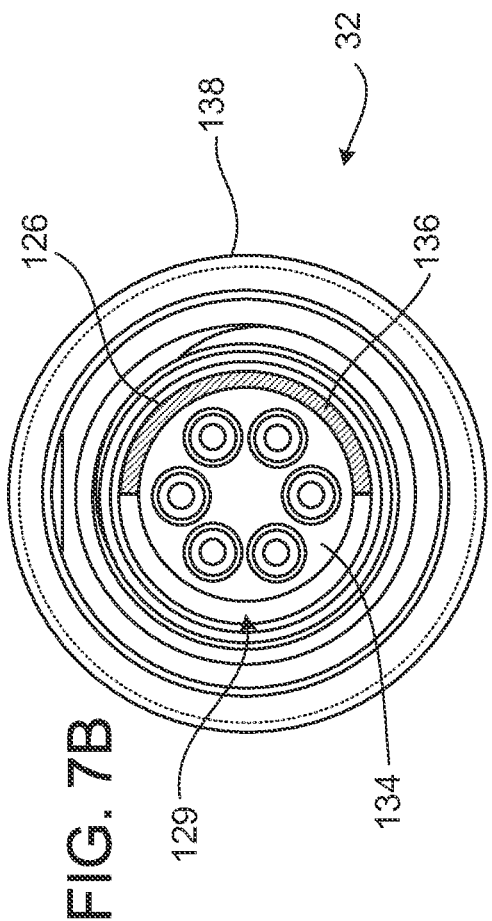
FIG. 7A
FIG. 7B

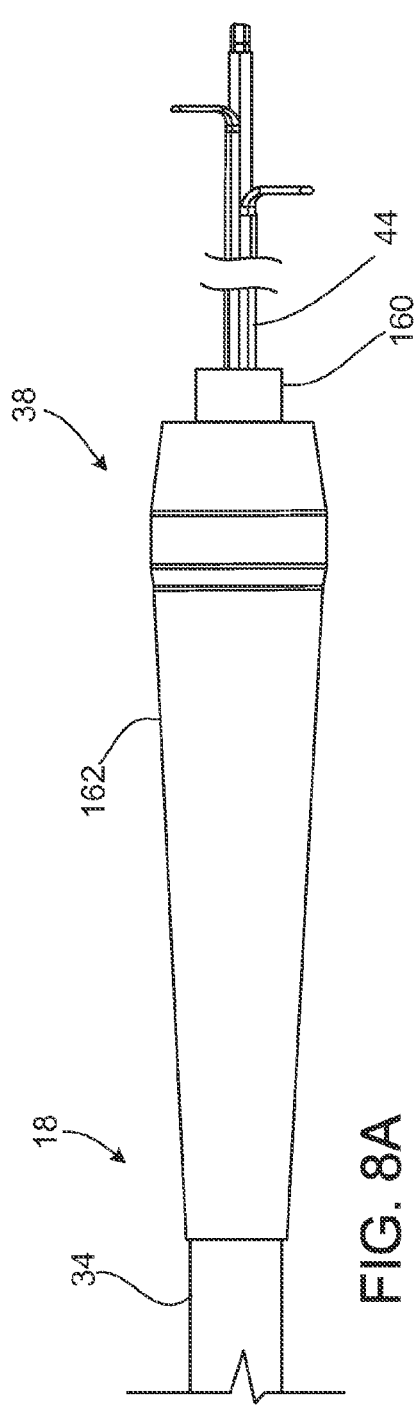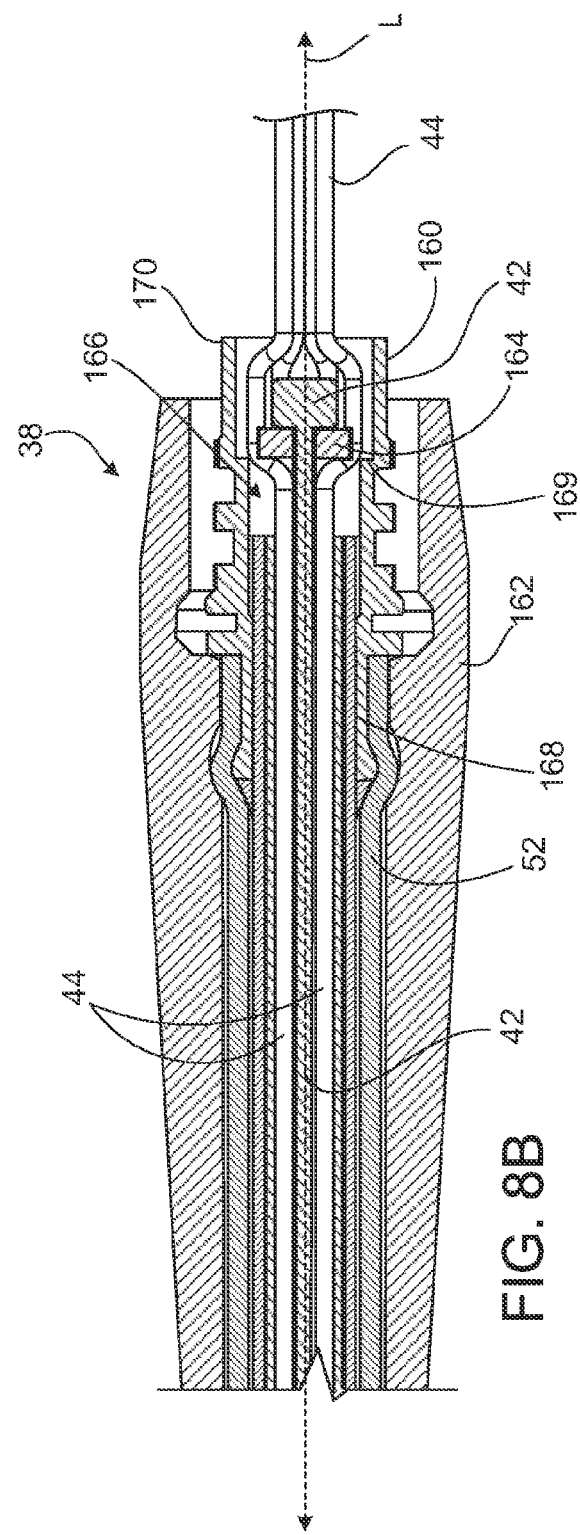

MODULAR DRIVELINE

CROSS-REFERENCE TO RELATED APPLICATION

The present application is a Continuation of U.S. Ser. No. 13/314,806 filed Dec. 8, 2011 (Allowed), which application claims the benefit of U.S. Provisional Appln. No. 61/420,908 filed Dec. 8, 2010; the full disclosures which are incorporated herein by reference in their entirety for all purposes.

TECHNICAL FIELD

This disclosure relates to modular cables, for example, modular drivelines for mechanical circulatory cardiac assist devices.

BACKGROUND

Heart assist devices or pumps can be inserted in the circulatory system to pump blood from the ventricle to the vasculature. Such a pump is known as a ventricular assist device, or VAD. A VAD is useful when the ventricle alone is incapable of providing adequate blood flow.

SUMMARY

A cable for supplying power and control signals to an implantable device includes a percutaneous portion and a modular portion. The percutaneous portion is configured to extend through an opening in a patient's body. The modular portion is removable from and re-attachable to the percutaneous portion.

A cable includes an inner member, conductors disposed about the inner member, a covering about the conductors, a layer extruded onto the covering, an armor braid over the extruded layer, and an outer jacket extruded over the armor braid.

Implementations can include one or more of the following features. For example, the covering includes a tape wrapped about the conductors, and the tape includes polytetrafluoroethylene. The layer extruded onto the tape includes thermoplastic polyurethane. The armor braid includes a fiber braided directly onto the extruded layer, wherein the fiber is selected from the group consisting of an aramid fiber and a para-aramid fiber. The braid tension of the armor braid is between 0 and 200 g. The armor braid has a number of carrier intersections between 5 and 12 carrier crossings per inch. The cable has a percutaneous portion, and the outer jacket of the percutaneous portion includes silicone. The cable has a modular portion, and the outer jacket of the modular portion includes thermoplastic polyurethane.

A connector includes a housing that houses one or more electrical contacts and a nut captured about the housing and non-threadedly, rotatably and axially movable relative to the housing, the nut including an element that engages an outer surface of the housing such that there is differential resistance to rotation of the nut depending on the direction of rotation, the nut configured to affix the connector to a second connector, wherein axial movement of the nut relative to the housing permits electrical connection between the connector and the second connector prior to the nut affixing the connectors.

Implementations can include one or more of the following features. For example, the element is configured to engage the outer surface such that the resistance is greater in a direction of rotation of the nut that detaches the nut from the second connector than in a direction of rotation of the nut that affixes the nut to the second connector. The element includes a rounded surface, and the outer surface of the housing includes a plurality of notches that receive the element. The rounded surface engages the notches to transmit a circumferential force along the nut during rotation of the nut, and the circumferential force is greater during rotation of the nut that detaches the nut from the second connector than during rotation of the nut that attaches the nut to the second connector. The outer surface is configured to deflect the element away from the housing. The housing defines a circumferential recess adjacent to the outer surface, the circumferential recess being configured to receive the element at a particular axial position of the nut relative to the housing.

A modular driveline includes a modular portion including a cable and a connector, the cable having terminations, and a percutaneous portion including a cable and a connector, the cable having terminations, the percutaneous portion connector for coupling to the modular portion connector, where all cable terminations at the connectors are captured in the connectors by potting.

Implementations can include one or more of the following features. For example, the modular portion includes a cable core, an armor braid, and an outer jacket. The armor braid flares outward from the cable core within the modular portion connector such that potting is received between the armor braid and the cable core. The cable core includes an inner member, and the inner member includes a knot in the modular portion connector. The inner member passes through a retaining member disposed in the modular portion connector. The retaining member has a generally spherical shape and defines a hole to admit the inner member. The cable core includes conductors and the modular portion connector includes contacts, and the conductors are disposed about the retaining member such that the ends of the conductors are axially aligned with respective contacts in the modular portion connector. The modular portion connector includes a housing secured to a cap by a threaded connection. The cap defines openings through which potting can be introduced. A bend relief is overmolded onto a portion of the cable and a portion of the modular portion connector.

The details of one or more implementations are set forth in the accompanying drawings and the description below. Other features, objects, and advantages will be apparent from the description and drawings, and from the claims.

DESCRIPTION OF DRAWINGS

FIG. 3A is a side view of a controller connector of a modular portion of the driveline.

FIG. 3B is an axial view of the controller connector of the modular portion.

FIG. 4A is a side view of an in-line connector of the modular portion.

FIG. 4B is an axial view of the in-line connector of the modular portion.

FIG. 7A is a side view of a distal connector of a percutaneous portion of the driveline.

FIG. 7B is an axial view of the distal connector of the percutaneous portion.

FIG. 8A is a side view of a proximal end of the percutaneous portion.

FIG. 8B is a side cutaway view of the proximal end of the percutaneous portion.

DETAILED DESCRIPTION

Figure 1:
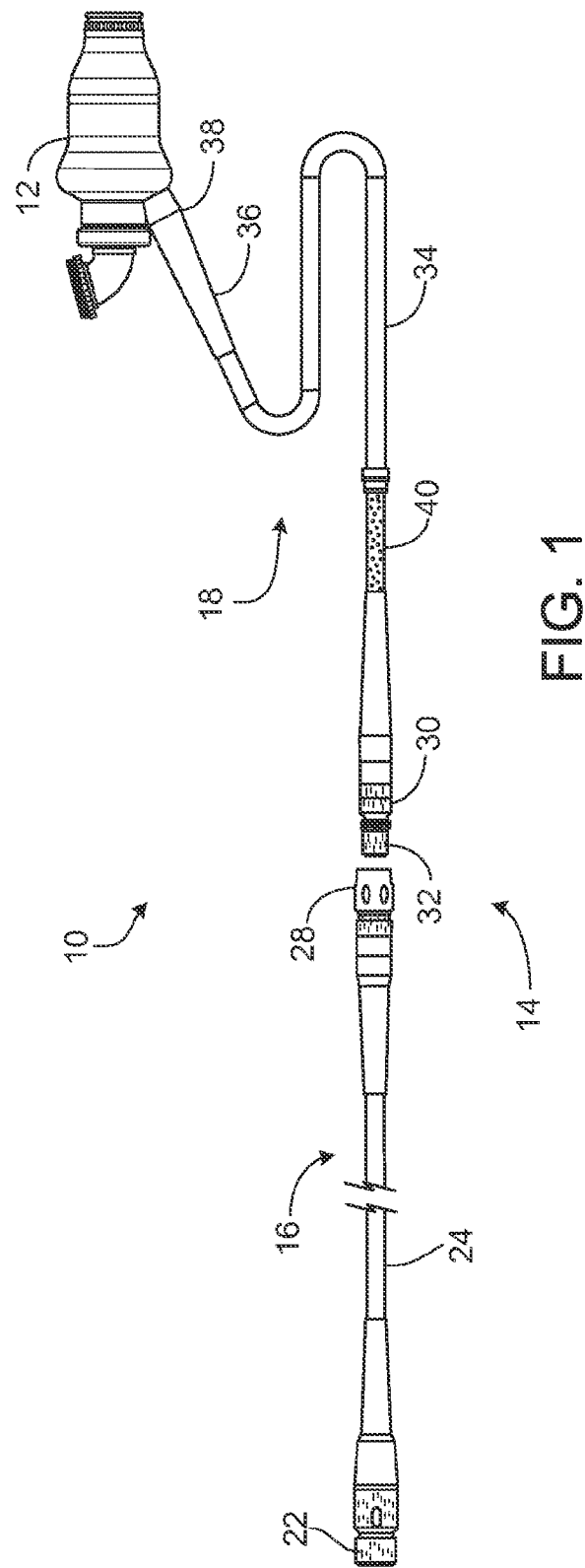
FIG. 1 is an illustration of a ventricular assist system including a modular driveline.

Referring to FIG. 1, a ventricular assist system 10 for treating, for example, a patient with a weakened left ventricle, includes a pump 12 and a driveline or cable 14. The terms driveline 14 and cable 14 may be used interchangeably. The driveline or cable 14 includes a modular portion 16 and a percutaneous portion 18 that are detachably coupled. The majority of the percutaneous portion 18 is implanted in a patient, while the modular portion 16 remains external to the patient. Because the modular portion 16 can be separated from the percutaneous portion 18, the modular portion 16 is easily replaceable in the event of wear or damage to the modular portion 16.

The driveline or cable 14 refers to the entire assembly that connects the pump 12 to a pump controller (not shown). The percutaneous portion 18 couples directly to the pump 12, and the modular portion 16 couples directly to the pump controller. Throughout the disclosure, the heart of the patient is used as a reference point. A portion of the driveline or cable 14 that is near the patient's heart is referred to as "proximal," whereas a portion far from the patient's heart is referred to as "distal." For example, the percutaneous portion 18 includes a proximal end 36 that is close to the patient's heart, and a distal end 30 that is farther from the patient's heart when the percutaneous portion 18 has been implanted in the patient.

The modular portion 16 includes a cable 24 attached to a controller connector 22 and an in-line connector 28. The controller connector 22 connects the modular portion 16 to the pump controller (not shown), and the in-line connector 28 connects the modular portion 16 to the percutaneous portion 18. The percutaneous portion 18 includes a cable 34 attached to a distal connector 32 and a proximal connector 38. The distal connector 32 connects the percutaneous portion 18 to the in-line connector 28 of the modular portion 16, and the proximal connector 38 is permanently or removably affixed to the pump 12. The percutaneous cable 34 also includes a velour outer portion 40 near the distal connector 32 that promotes tissue ingrowth and can be formed, for example, of polyester.

Figure 2:
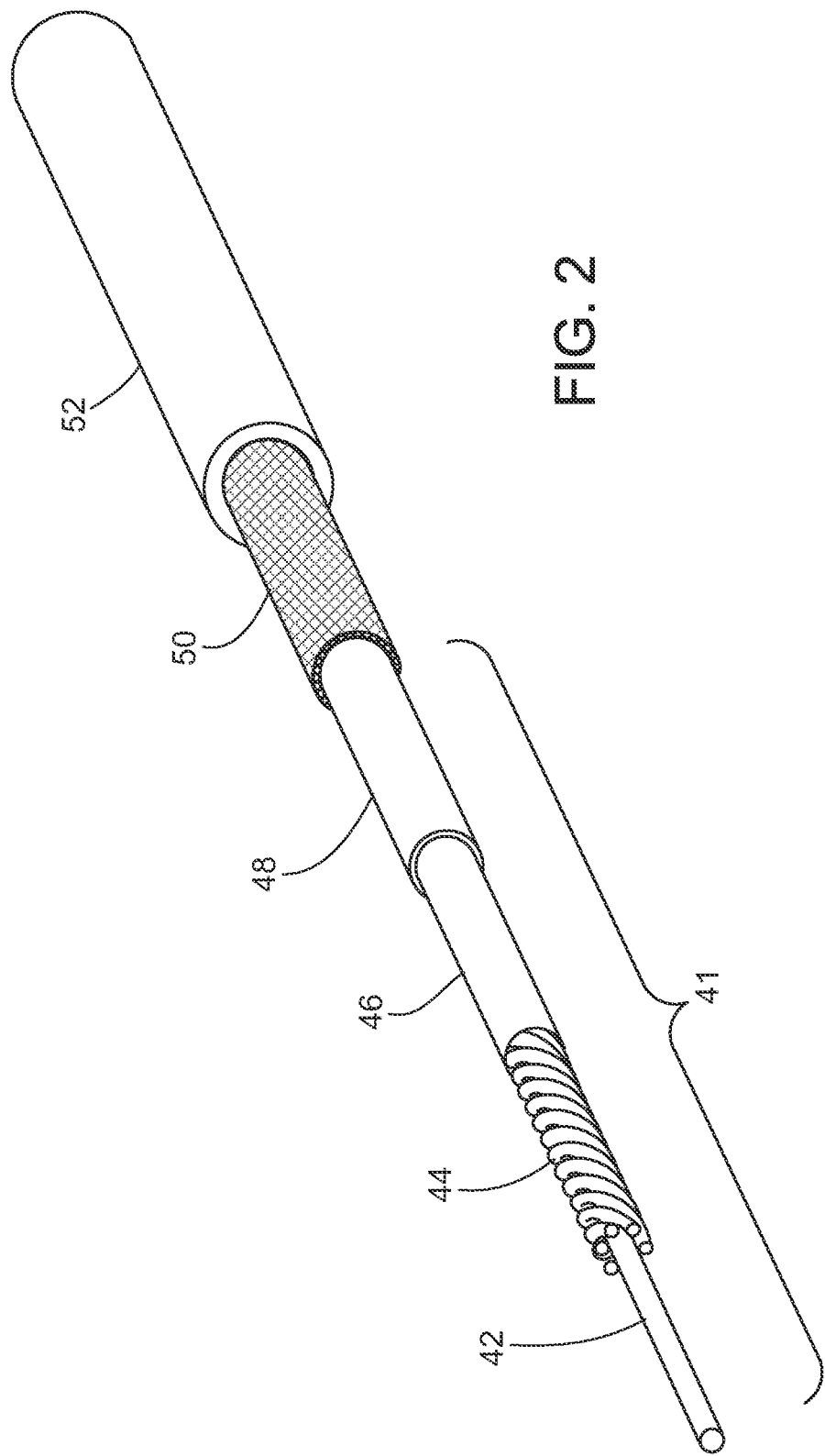
FIG. 2 is a cutaway view of a cable of the driveline.

Referring to FIG. 2, both the modular cable 24 and the percutaneous cable 34 include a cable core 41. The cable core 41 includes an inner strength member 42 formed, for example, of braided polyethelene, to provide resistance to axial breakage. Disposed about the inner strength member 42 are conductors 44 that carry power and data between the pump controller and the pump 12. The conductors 44 can be wrapped helically, or wrapped in twisted pairs, or arranged in other configurations known to those skilled in the art about the inner strength member 42. Here, six conductors 44 are shown, but more or fewer conductors 44 can be included. Wrapped over the conductors 44 is a covering 46 that provides lubricity between the conductors and other layers. For example, the covering 46 can include a tape wrapped over the conductors 44 to reduce friction, thereby increasing the longevity of the cable. The covering 46 can be formed, for example, of polytetrafluoroethylene (PTFE). Over the covering 46, there is a layer 48 of, for example, thermoplastic polyurethane that is extruded directly onto the covering 46, completing the cable core 41. The layer 48 may also be formed of, for example, a polycarbonate-urethane, a silicone polycarbonate-urethane, or other thermoplastics and copolymers. The covering 46 provides a barrier so that the layer 48 can be extruded close to the conductors 44 but not seep in between the conductors 44. The covering 46 also provides a generally smooth surface to receive the extruded layer 48 and acts as a thermal barrier during extrusion of the layer 48.

Located over the cable core 41 and braided directly over the extruded layer 48, is an armor braid 50 that provides resistance to cuts, flexure failure, and other damage. The armor braid 50 includes, for example, between 16 and 32 carriers, with 24 carriers being preferred. The carriers are braided together with a tension of between 0 and 200 grams, or more specifically, between 20 and 120 grams. The armor braid 50 is formed with between 5 and 12 carrier crossings per inch, and in one embodiment, between 7 and 9 carrier crossings per inch. The carriers are formed of, for example, an aramid fiber or a para-aramid fiber.

Extruded directly onto the armor braid 50 is an outer jacket 52. The outer jacket 52 is extruded such that the material of the outer jacket 52 enters the surface features of the armor braid 50 but does not penetrate the armor braid 50. The extrusion process results in an air gap between the outer jacket 52 and the armor braid 50 of less than 0.1 inch, and in one embodiment, between 0 and 0.05 inches. The outer jacket 52 may be formed so that there is no air gap between the outer jacket 52 and the armor braid 50. The outer jacket 52 of the modular cable 24 is formed, for example, of a thermoplastic polyurethane, and the outer jacket 52 of the percutaneous cable 34 is formed, for example, of a silicone elastomer.

Referring to FIG. 3A, the modular portion 16 includes a bend relief 54 that reinforces the connection of the modular cable 24 to the controller connector 22. The bend relief 54 is formed, for example, of a thermoplastic polyurethane molded directly over a portion of the modular cable 24 and a portion of the controller connector 22. Portions of the modular cable 24 and the controller connector 22 are grit-blasted and primed in preparation to receive the overmolded bend relief 54. The bend relief 54 includes recesses 57 that extend through the bend relief 54 to the outer jacket 52 of the modular cable 24. The recesses 57 reduce the stiffness for a portion of each bend relief 54, which enables a gradual transition in stiffness from the cable 24 to the controller connector 22. In addition to the proportions illustrated, the recesses 57 can have a smaller width in an axial direction, increased or decreased corner radii, and greater or smaller depth in a direction perpendicular to the axis of the cable. The bend relief 54 can also include more or fewer recesses 57 than those illustrated.

The geometry and dimensions of the bend relief 54 can affect the longevity of the controller connector 22. The width of the recesses 57 (in a direction along the longitudinal axis, L) can be between approximately 0 and 0.2 inches, or between approximately 0.02 to 0.15 inches. The corner radius of the recesses 57 can be between 0 to 0.1 inches, or between approximately 0 to 0.7 inches.

The bend relief 54 can include circumferential ribs 61 that extend about a portion of the circumference of the bend relief 54 and are spaced along the length of the bend relief 54. The width of the circumferential ribs 61 (in a direction along the longitudinal axis, L) can be between approximately 0 and 0.3 inches, or between approximately 0.05 to 0.25 inches. The bend relief 54 can include between approximately 0 and 20 or between 5 and 15 circumferential ribs 61.

Connecting the circumferential ribs 61, the bend relief 54 includes axial ribs 63 that extend in the direction of the longitudinal axis, L of the bend relief 54. The width of the axial ribs 63 (in a circumferential direction about the bend relief 54) can be between approximately 0 to the full circumference of the bend relief 54, or between approximately 0.05 to 0.25 inches. The number of axial ribs 63 can vary based on the position along the length of the bend relief 54. Portions near the ends of the bend relief 54 can include between approximately 0 and 6 axial ribs 63 or between approximately 0 and 4 axial ribs 63 at a given position along the longitudinal axis, L. A middle portion of the bend relief 54 can include between approximately 0 and 8 or between approximately 0 and 6 axial ribs 63.

The height of the ribs 61, 63 (in a direction radially outward from the cable 24) can vary according to the taper angle of the bend relief 54. The axial ribs 63 and the circumferential ribs 61 can have a height of between approximately 0 and 2 times the general taper height of the bend relief 54, or between approximately one half to one and a half times the general taper height of the bend relief 54.

Figure 3C:
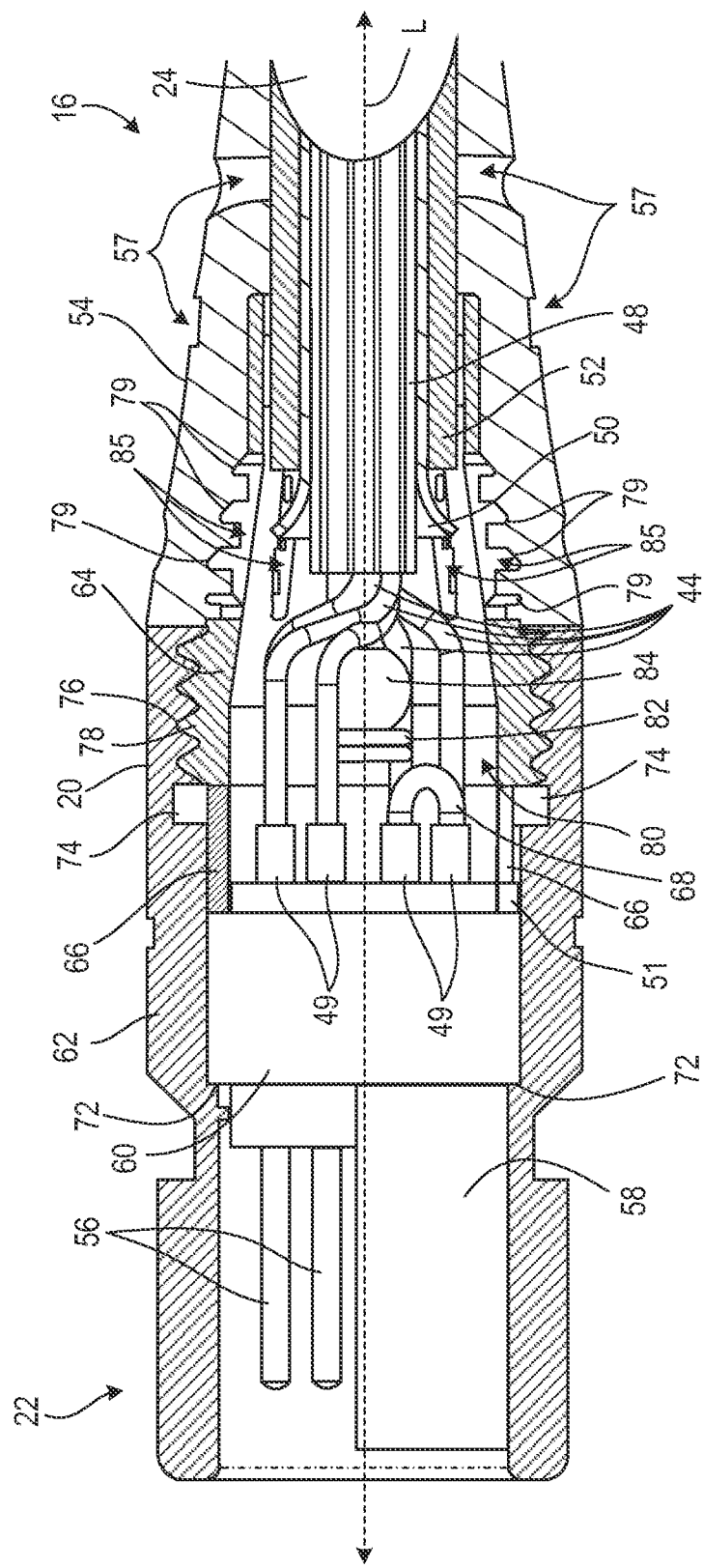
FIG. 3C is a side cutaway view of the controller connector of the modular portion.

Referring to FIG. 3B, the controller connector 22 includes eight pins 56 to electrically connect the modular portion 16 to the pump controller, but a configuration with more or fewer pins could also be used. Six of the pins 56 can connect with the six conductors 44 of the modular cable 24, and two of the pins 56 can connect to other components of the controller connector 22 as will be described in greater detail below. The controller connector 22 includes an alignment rim 58 (see also FIG. 3C) disposed partially circumferentially around the pins 56 that provides radial alignment of the controller connector 22 with a socket of the pump controller.

Referring to FIG. 3C, the controller connector 22 includes a housing 62 that receives a cap 64. The housing 62 includes an inner threaded region 76 and a circumferential engagement surface 72 that limits travel of a connector body 60 and a spacer 66 within the housing 62. The housing 62 can define a circumferential thread relief 74, for example, a recess defined near the threaded region 76. Incompletely-formed threads of the threaded region 76 can be removed, thereby defining the thread relief 74. The cap 64 (see also FIG. 3D) includes an outer threaded region 78 and ridges 79. The threaded region 78 of the cap 64 engages the threaded region 76 of the housing 62 to couple the cap 64 to the housing 62. The threaded region 78 of the housing 62 and the threaded region 76 of the cap 64 can be secured by a thread-locking adhesive or a weld. The ridges 79 of the cap 64 remain outside the cap 64 and secure the bend relief 54 of the controller connector 22.

The controller connector 22 also includes the connector body 60 and the spacer 66, which are both located within the housing 62. The connector body 60 and the spacer 66 are secured between the cap 64 and the engagement surface 72 of the housing 62. The connector body 60 is coupled to the pins 56 and the alignment rim 58 of the controller connector 22. The connector body 60 includes contacts 49 that receive the conductors 44 of the modular cable 24. In one embodiment, two of the contacts 49 are joined by a jumper 68 to electrically connect two of the pins 56. The jumper 68 enables the pump controller to detect that the controller connector 22 is attached, by, for example, periodically testing whether a circuit is completed by the presence of the jumper 68.

The connector body 60 is positioned between the spacer 66 and the engagement surface 72 of the housing 62. The spacer 66 enables consistent pressure to be applied to the end of the connector body 60. The spacer 66 transmits force from the cap 64 along the longitudinal axis, L. The spacer 66 is formed in the shape of a hollow cylinder with gap 53 defined in the side of the spacer 66 (see also FIG. 3E). The gap 53 of the spacer 66 admits an uneven feature of the connector body, such as a key 51, enabling the cap 64 to evenly exert pressure through the spacer 66 to the connector body 60. The spacer 66 enables force to be exerted beyond the end of the cap 64, for example, past the thread relief 74.

The spacer 66 and the cap 64 define a solder pocket 80 (e.g., a chamber) in which the elements of the modular cable 24 are terminated. The ends of the solder pocket 80 are defined by the connector body 60 and the modular cable 24. The cable core 41, armor braid 50, and outer jacket 52 all enter the solder pocket 80 straight along the longitudinal axis, L. Because the elements of the modular cable 24 enter the cap 64 in this direction, the modular cable 24 can be terminated in a way that enables the controller connector 22 to have a small outer diameter, for example, in the range of about one quarter of an inch to about three-quarters of an inch. In one embodiment, the inner strength member 42 terminates at an end 82 that passes through a retention ball 84 and is knotted to prevent the end 82 of the inner strength member 42 from slipping. The retention ball 84 has a generally spherical shape and defines a hole to admit the inner strength member 42. Alternatively, the inner strength member 42 can be secured using no knots or multiple knots. Instead of a retention ball 84, a retaining member of another shape can be used.

The conductors 44 bend around the retention ball 84 and attach to the contacts 49 of the connector body 60 to electrically connect with respective pins 56. To reduce stress on the conductors 44, the conductors can be aligned with their respective contacts 49 so that the conductors 44 do not cross each other unnecessarily. The armor braid 50 flares outward from the cable core 41 in the solder pocket 80 to receive potting material between the armor braid 50 and the extruded layer 48 to secure the armor braid 50 within the solder pocket 80.

Figure 3D:
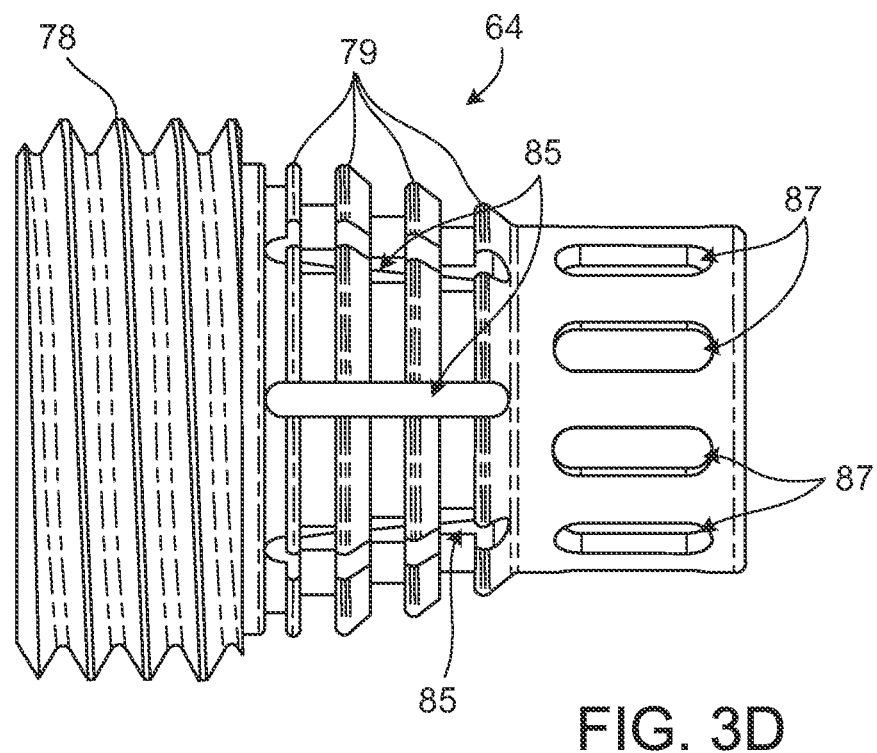
FIG. 3D is a side view of a cap of the controller connector of FIG. 3A.
Figure 3E:
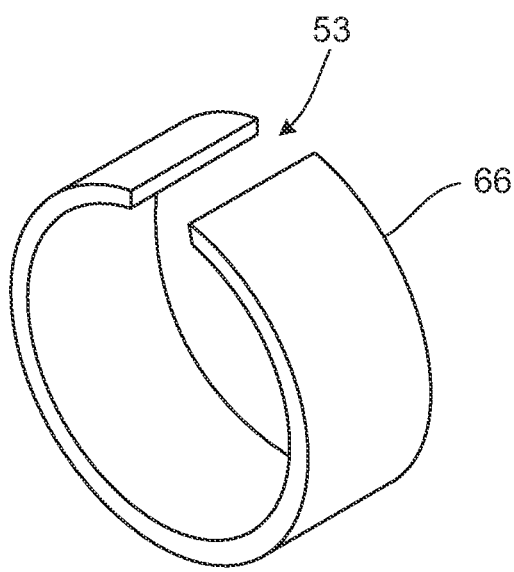
FIG. 3E is a perspective view of a spacer of the controller connector of FIG. 3A.

To anchor the terminations of the modular cable 24, a potting material of, for example, high-strength epoxy is introduced into the solder pocket 80. As shown in FIG. 3D, the cap 64 defines openings 85 and slots 87. Potting material is introduced into the solder pocket 80 through the openings 85 in the cap 64, and air in the solder pocket 80 can escape through the openings 85. The potting material is cured, for example, by ultraviolet light, and when hardened, secures the conductors 44, the end 82 of the inner strength member 42, the flared end of the armor braid 50, and other terminations of the modular cable 24. The hardened epoxy resists becoming dislodged or deformed when axial loads are exerted on the modular cable 24.

The bend relief 54 is overmolded onto the controller connector 22 after the potting is cured. The slots 87 defined in the cap 64 permit overmolded material of the bend relief 54 to flow through the cap 64 and connect to the outer jacket 52. The material that flows through the slots 87 helps lock the bend relief 54 to the cap 64.

Referring to FIG. 4A, the modular portion 16 includes a bend relief 55 that reinforces the connection of the modular cable 24 to the in-line connector 28. The bend relief 55 is formed, for example, of a thermoplastic polyurethane molded directly over a portion of the modular cable 24 and a portion of the in-line connector 28. Portions of the modular cable 24 and the in-line connector 28 are grit-blasted and primed in preparation to receive the overmolded bend relief 55. The bend relief 55 includes recesses 59 that extend through the bend relief to the outer jacket 52 of the modular cable 24. The recesses 59 reduce the stiffness for a portion of the bend relief 55, which enables a gradual transition in stiffness from the cable 24 to the in-line connector 28. In addition to the proportions illustrated, the recesses 59 can have a smaller width in an axial direction, increased or decreased corner radii, and greater or smaller depth in a direction perpendicular to the axis of the cable. The bend relief 55 can also include more or fewer recesses 59 than those illustrated.

The geometry and dimensions of the bend relief 55 can affect the longevity of the in-line connector 28. The width of the recesses 59 (in a direction along the longitudinal axis, L) can be between approximately 0 and 0.2 inches, or between approximately 0.02 to 0.15 inches. The corner radius of the recesses 59 can be between 0 to 0.1 inches, or between approximately 0 to 0.7 inches.

The bend relief 55 can include circumferential ribs 65 that extend about a portion of the circumference of the bend relief 55 and are spaced along the length of the bend relief 55. The width of the circumferential ribs 65 (in a direction along the longitudinal axis, L) can be between approximately 0 and 0.3 inches, or between approximately 0.05 to 0.25 inches. The bend relief 55 can include between approximately 0 and 20 or between 5 and 15 circumferential ribs 65.

Connecting the circumferential ribs 65, the bend relief 55 includes axial ribs 67 that extend in the direction of the longitudinal axis, L of the bend relief 55. The width of the axial ribs 67 (in a circumferential direction about the bend relief 55) can be between approximately 0 to the full circumference of the bend relief 55, or between approximately 0.05 to 0.25 inches. The number of axial ribs 67 can vary based on the position along the length of the bend relief 55. Portions near the ends of the bend relief 55 can include between approximately 0 and 6 axial ribs 67 or between approximately 0 and 4 axial ribs 67 at a given position along the longitudinal axis, L. A middle portion of the bend relief 55 can include between approximately 0 and 7 or between approximately 0 and 5 axial ribs 67.

The height of the ribs 65, 67 (in a direction radially outward from the cable 24) can vary according to the taper angle of the bend relief 55. The axial ribs 67 and the circumferential ribs 65 can have a height of between approximately 0 and 2 times the general taper height of the bend relief 55, or between approximately one half to one and a half times the general taper height of the bend relief 55.

Referring to FIG. 4B, the in-line connector 28 of the modular portion 16 includes an alignment rim 94 for radial alignment of the in-line connector 28 with the distal connector 32. The in-line connector 28 also includes six pins 92 that engage a socket of the distal connector 32 of the percutaneous portion 18. Because pins 92 are more likely to be damaged than a socket, the pins 92 are included in the in-line connector 28, which is included in the module portion 16. If the pins become damaged, the modular portion 16 can be replaced more easily than the implanted percutaneous portion 18. Nevertheless, in an alternative implementation, the in-line connector 28 can include a socket and the distal connector 32 can include corresponding pins.

Figure 4C:
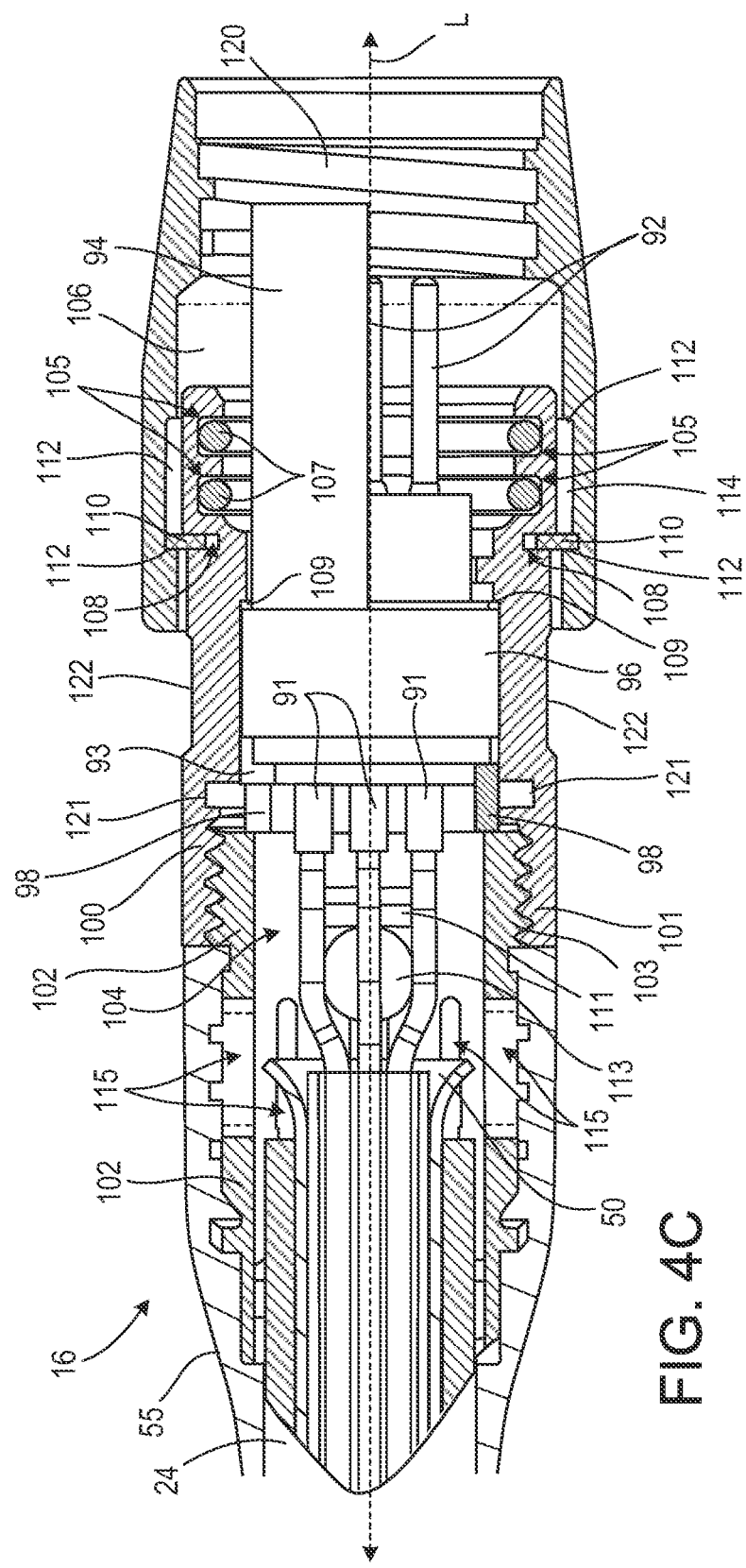
FIG. 4C is a side cutaway view of the in-line connector of the modular portion.

Referring to FIG. 4C, the in-line connector 28 includes a housing 100 that receives a cap 102. The housing 100 includes an inner threaded region 101 and a circumferential engagement surface 109 that limits travel of a connector body 96 and a spacer 98 within the housing 100. The housing 100 can define a circumferential thread relief 121, for example, a recess defined near the threaded region 101. Incompletely-formed threads of the threaded region 101 can be removed, thereby defining the thread relief 121. The housing 100 defines two radial grooves 105 in which o-rings 107 are placed to seal the connection between the in-line connector 28 of the modular portion 16 and the distal connector 32 of the percutaneous portion 18. The placement of the o-rings 107 along the axis of the housing 100 enables the electrical connection to be established between the in-line connector 28 and the distal connector 32 before the engagement of the o-rings 107 engage the distal connector 32. Thus any force by the o-rings 107 that resists connection of the distal connector 32 and the in-line connector 28 occurs after the electrical connection is established.

Figure 4D:
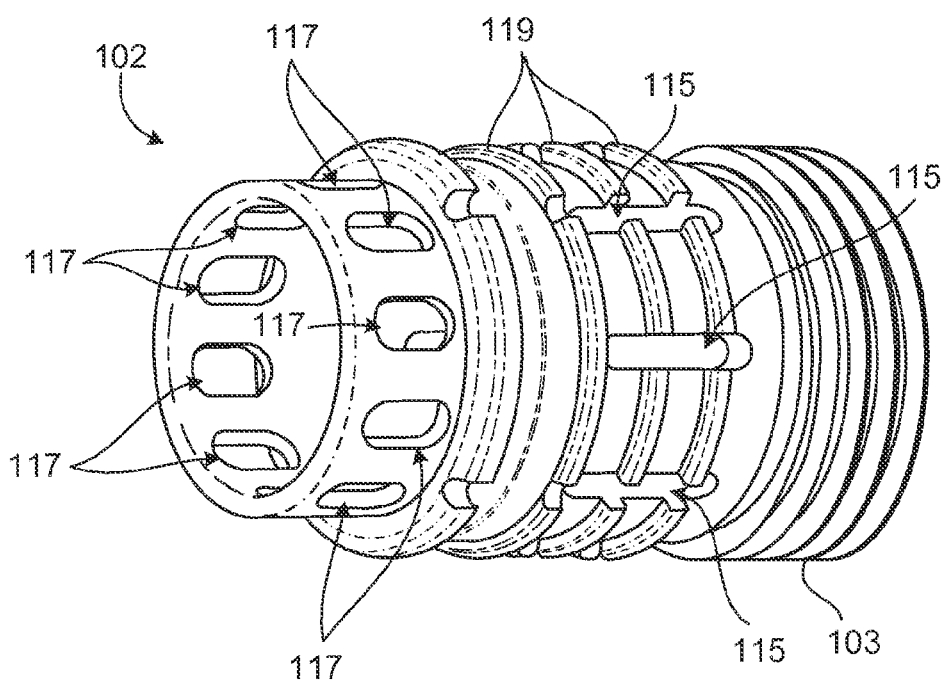
FIG. 4D is a perspective view of a cap of the in-line connector of FIG. 4A.

Referring to FIG. 4D, the cap 102 includes an outer threaded region 103 and ridges 119. The threaded region 103 of the cap 102 engages the threaded region 101 of the housing 100 to couple the cap 102 to the housing 100. The threaded region 101 of the housing 100 and the threaded region 103 of the cap 102 can be secured by a thread-locking adhesive or a weld. The ridges 119 of the cap 102 remain outside the housing 100 and secure the bend relief 55 of the in-line connector 28.

Referring now to FIG. 4C, the in-line connector 28 also includes the connector body 96 and the spacer 98, which are both located within the housing 100, secured between the cap 102 and the engagement surface 109 of the housing 100. The connector body 96 is coupled to the pins 92 and the alignment rim 94. The connector body 96 also includes contacts 91 that receive the conductors 44 of the modular cable 24. The connector body 96 is positioned between the engagement surface 109 of the housing 100 and the spacer 98. In the assembled in-line connector 28, the pins 92 (which are the electrical contacts of the in-line connector 28) are secured to the housing 100. The pins 92 are disposed, for example, partially within the housing 100 and extend partially out of the housing 100.

Figure 4E:
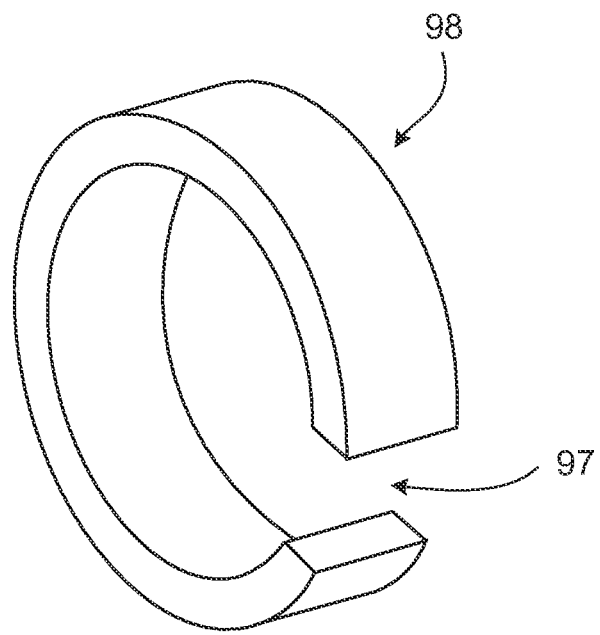
FIG. 4E is a perspective view of a spacer of the in-line connector of FIG. 4A.

The spacer 98 (also shown in FIG. 4E) is formed in the shape of a hollow cylinder with a gap 97 defined in the side of the spacer 98. The gap 97 of the spacer 66 admits an uneven feature of the connector body 96, such as a key 93. The spacer 98 transmits force from the end of the cap 102 to the end of the connector body 96.

The spacer 98 and the cap 102 define a solder pocket 104 (e.g., a chamber) in which the elements of the modular cable 24 are terminated. The ends of the solder pocket 104 are defined by the connector body 96 and the modular cable 24. The cable core 41, armor braid 50, and outer jacket 52 all enter the solder pocket 104 straight along the longitudinal axis, L. Because the elements of the modular cable 24 enter the cap 102 in this direction, the modular cable 24 can be terminated in a way that enables the in-line connector 28 to have a small outer diameter, for example, in the range of approximately one quarter of an inch to about three-quarters of an inch. The inner strength member 42 terminates at an end 111 that passes through a retention ball 113 and is knotted to prevent the end 111 of the inner strength member 42 from slipping. The retention ball 113 has a generally spherical shape and defines a hole to admit the inner strength member 42. Alternatively, the inner strength member 42 can be secured using no knots or multiple knots. Instead of a retention ball 113, a retaining member of another shape can be used.

The conductors 44 bend around the retention ball 113 and attach to the contacts 91 of the connector body 96 to electrically connect with the pins 92. The armor braid 50 flares outward from the cable core 41 in the solder pocket 104 to receive potting material between the armor braid 50 and the extruded layer 48 to secure the armor braid 50 in the solder pocket 104.

To anchor the terminations of the modular cable 24, a potting material of, for example, high-strength epoxy is introduced into the solder pocket 104. The cap 102 defines openings 115 and slots 117 (see also FIG. 4D). Potting material is introduced into the solder pocket 104 through the openings 115 in the cap 102, and air in the solder pocket 104 can escape through the openings 115. The potting material is cured by ultraviolet light, and when hardened, secures the conductors 44, the end 111 of the inner strength member 42, the flared end of the armor braid 50, and other terminations of the modular cable 24. The hardened epoxy resists becoming dislodged or deformed when axial loads are exerted on the modular cable 24.

The bend relief 54 is overmolded onto the in-line connector 28 after the potting is cured. The slots 117 permit overmolded material of the bend relief 55 to flow through the cap 102 and connect to the outer jacket 52. The material that flows through the slots 117 helps lock the bend relief 55 to the cap 102.

The in-line connector 28 includes a nut 106 captured about the exterior of the housing 100. The nut 106 is configured to affix the in-line connector 28 to the distal connector 23. The nut 106 can rotate about the housing 100 and can move axially along the housing 100. The nut 106 is captured about the housing 100 in a non-threaded manner and thus can move non-threadedly relative to the housing 100.

Figure 4F:
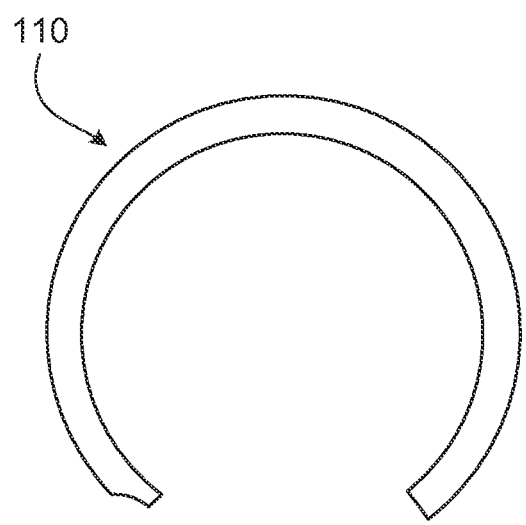
FIG. 4F is an axial view of a retaining member of the in-line connector of FIG. 4A.
Figure 5A:
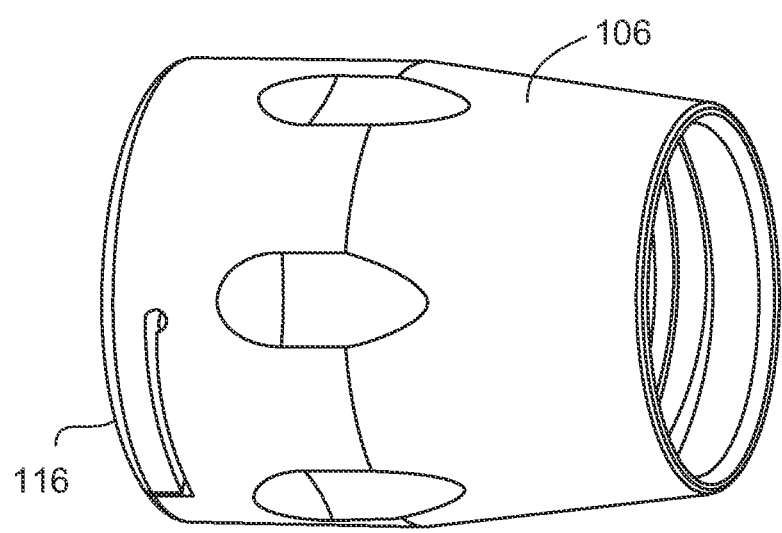
FIG. 5A is a perspective view of a nut of the in-line connector of FIG. 4A.
Figure 5B:
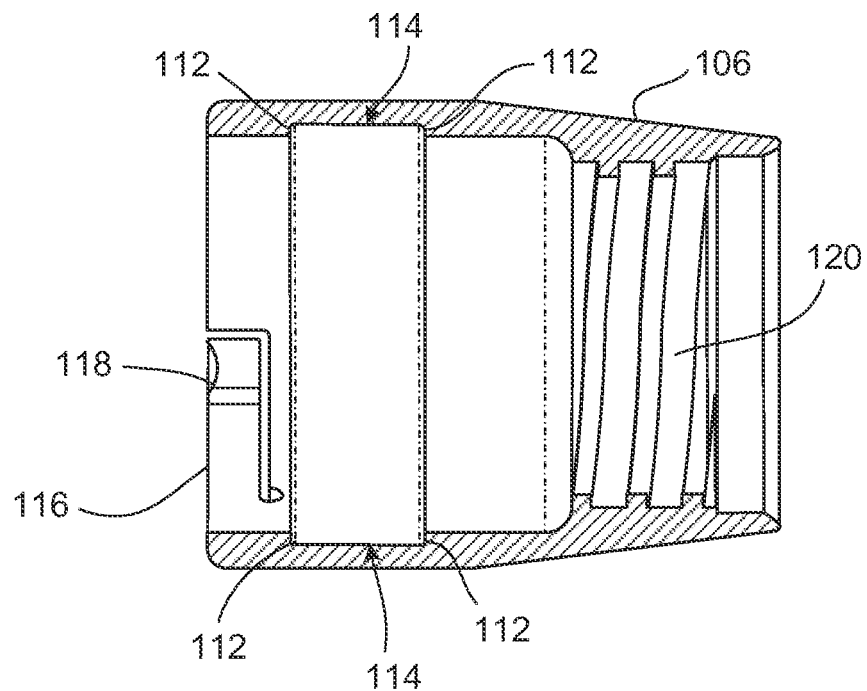
FIG. 5B is a cross-sectional view of the nut of FIG. 5A.

The nut 106 defines a circumferential recess 114 on the inner surface of the nut 106 between opposing circumferential walls 112 of the nut 106 (see also FIG. 5B). The housing 100 defines a circumferential groove 108 that receives a retaining member 110. The retaining member 110 (FIG. 4F) is formed in the shape of a thin, circular arc, and has an outer diameter slightly larger than the outer diameter of the housing 100. Because the retaining member 110 is not a complete circle, the retaining member 110 can flex to enter the groove 108, which allows the nut 106 to be positioned around the housing 100. Once the nut 106 is in place, the retaining member 110 expands into the recess 114 to capture the nut 106. In the assembled in-line connector 28, the retaining member 110 is partially disposed in the groove 108 of the housing 100 and partially disposed in the recess 114 of the nut 106.

The length of the recess 114 along the longitudinal axis, L, allows the nut 106 to travel longitudinally relative to the housing 100, with the travel being limited by the retaining member 110 engaging one of the opposing walls 112. Because the nut 106 can travel a distance along the longitudinal axis, L, the nut 106 does not impede connection of the pins 92 to the distal connector 32 of the percutaneous portion 18. As a result, the in-line connector 28 can connect electrically to the distal connector 32 before the nut 106 is secured to the distal connector 32, as described below.

Figure 5C:
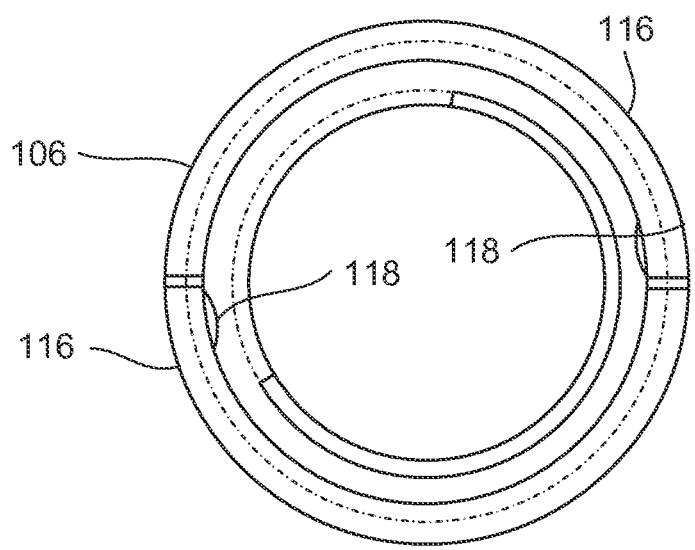
FIG. 5C is an axial view of the nut of FIG. 5A.

Referring to FIGS. 5A to 5C, the nut 106 includes a threaded inner surface 120 to engage the distal connector 32 of the percutaneous portion 18. The nut 106 also includes two cantilevered elements 116 that are integral to the nut 106. At the end of each element 116, a protrusion 118 is formed. Each protrusion 118 includes a rounded surface. The protrusions 118 inwardly extend toward the interior of the nut 106 to engage an outer surface of the housing 100.

Figure 6A:
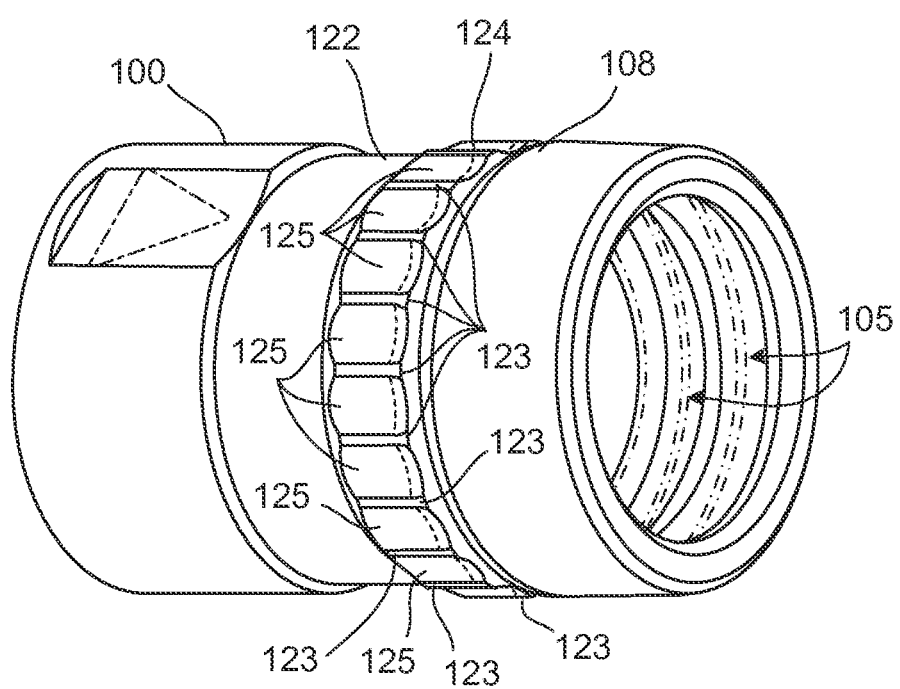
FIG. 6A is a perspective view of a housing of the in-line connector of FIG. 4A.
Figure 6B:
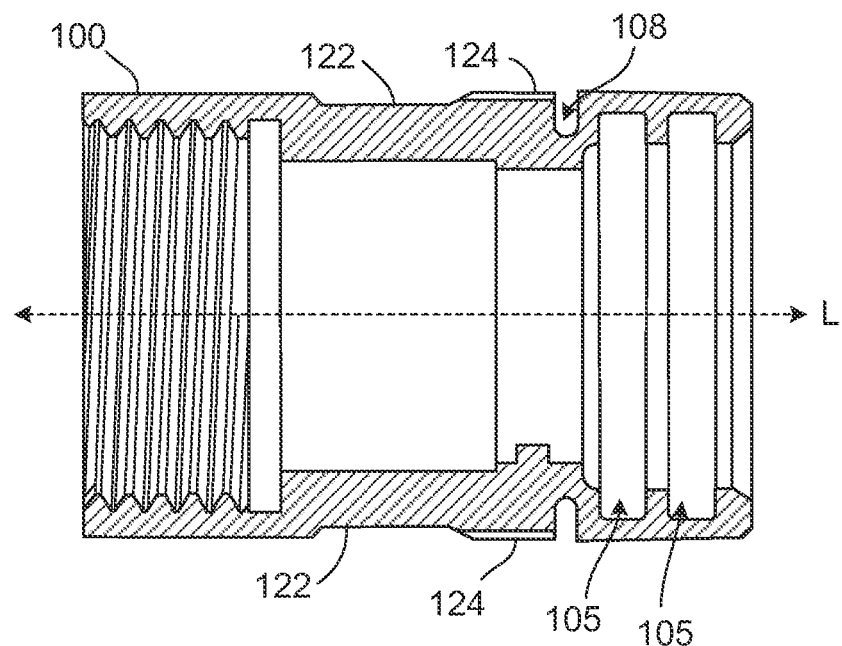
FIG. 6B is a cross-sectional view of the housing of FIG. 6A.
Figure 6C:
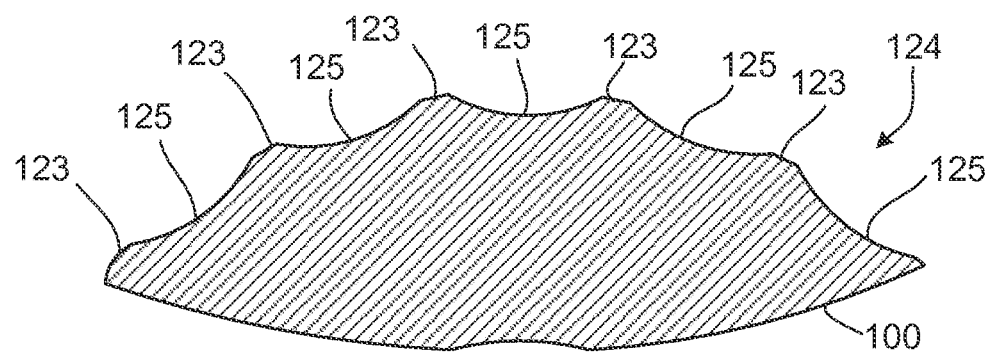
FIG. 6C is a view of a notched portion of the housing of FIG. 6A.

Referring to FIGS. 6A to 6C, the exterior of the housing 100 includes a circumferential recess 122 and a circumferential outer surface 124. The circumferential recess 122 is located adjacent to the outer surface 124. The outer surface 124 includes a plurality of notches 125 that receive the element 116. Between the notches 125, a plurality of ridges 123 are formed on the outer surface 124. The notches 125 can control the relative ease of the movement of the cantilevered elements 116 in different directions. The notches 125 can be even and symmetric (as shown) or the notches 125 can be biased and asymmetrical. The symmetric notches 125 illustrated can provide greater resistance to rotation of the nut 106 in one direction than in the opposite direction.

In the assembled in-line connector 28, the nut 106 is positioned about the housing 100 with the elements 116 of the nut 106 positioned over either the circumferential recess 122 or the outer surface 124, depending on the longitudinal position of the nut 106 relative to the housing 100. For approximately half of the travel of the nut 106 relative to the housing 100, the elements 116 are positioned over the circumferential recess 122 and rotation of the nut 106 is essentially without resistance. As a result, a person who is unfamiliar with the operation of the in-line connector 28 can initiate the engagement of the nut 106 to the distal connector 32 with confidence. Having begun the rotation without resistance, a person is more likely to be comfortable continuing the rotation of the nut 106 to fully connect the in-line connector 28 to the distal connector 32, even after a degree of resistance is provided approximately halfway through the engagement of the nut 106 to the distal connector 32. The threaded connection between the nut 106 and the threaded portion 128 also provides mechanical advantage, assisting the protrusions 118 to slide out of the notches 125 and over the ridges 123.

The configuration of the nut 106 about the housing 100 enhances the ability of the in-line connector 28 to connect with the distal connector 32. First, when the in-line connector 28 begins to engage the distal connector 32, the nut 106 can travel along the longitudinal axis, L, of the in-line connector 28. Axial movement of the nut 106 relative to the housing 100 in this manner permits electrical connection between the in-line connector 28 and the distal connector 32 prior to the nut 106 affixing the in-line connector 28 to the distal connector 32. For example, the nut 106 may move axially relative to the housing 100, permitting the pins 92 that are housed in the housing 100 of in-line connector 28 to enter the socket 134 of the distal connector 32 and establish electrical connections. As a result, power can flow from the pump controller to the pump 12 through the driveline or cable 14 before the nut 106 is fully engaged. When connecting the in-line connector 28 to the distal connector 32, a portion of the distal connector 32 can engage the nut 106 to cause the nut 106 to travel axially relative to the housing 100.

Second, the nut 106 can rotate freely about the housing 100 when the nut begins to engage the threaded portion 128 of the distal connector 32. For approximately the first portion of the engagement of the nut 106 to the distal connector, the elements 116 of the nut 106 are positioned over the circumferential recess 122 of the housing 100. For one or more axial positions of the nut 106 relative to the housing 100, the circumferential recess 122 receives the elements 116 and the protrusions 118 do not contact the housing 100. While the elements 116 are received in the circumferential recess 122, the elements 116 do not engage the outer surface 124, allowing the nut 106 to rotate freely around the housing 100.

Third, as the nut 106 continues to engage the distal connector 32, the nut 106 travels axially to a second position relative to the housing 100 at which the elements 116 engage the outer surface 124. The second position of the nut 106, at which resistance to rotation of the nut 106 is provided, may be reached when the nut 106 is partially affixed to the distal connector 32. Approximately halfway along the axial travel of the nut 106, the elements 116 of the nut 106 become positioned over the outer surface 124 of the housing 100 (instead of over the circumferential recess 122 of the housing 100), and the elements 116 engage the outer surface 124. In particular, the protrusion 118 on each element 116 settles in the notches 125 of the outer surface 124.

The engagement of the protrusions 118 with the outer surface 124 resists rotation of the nut 106 relative to the housing 100. During rotation of the nut 106 relative to the housing 100, as the protrusions 118 move out of the notches 125 and over the ridges 123 of the outer surface 124, the outer surface 124 deflects the elements 116 away from the housing 100. Force is also exerted circumferentially on the nut 106 along the length of each element 116. The circumferential force must be overcome to complete rotation of the nut 106 relative to the housing 100. The movement of the protrusions 118 over the outer surface 124 also provides a ratcheting effect as the nut 106 rotates.

Fourth, the in-line connector 28 provides differential resistance to rotation of the nut 106 depending on the direction of rotation of the nut 106 relative to the housing 100. The element 116 is configured to engage the outer surface 124 such that the resistance is greater in a direction of rotation of the nut 106 that detaches the nut 106 from the distal connector 32 than in a direction of rotation of the nut 106 that affixes the nut 106 to the distal connector 32. The increased resistance to detachment of the nut 106 discourages accidental disengagement of the in-line connector 28 from the distal connector 32.

To achieve the differential resistance, the protrusions 118 require a higher force to overcome friction from the notches 125 of the outer surface 124 during rotation of the nut 106 to detach the nut from the distal connector 32 compared to rotation of the nut 106 to affix the nut 106 to the distal connector 32. As the nut 106 rotates, the rounded surface of the protrusions 118 engages the notches 125 to transmit a circumferential force on the nut 106 through the elements 116. The circumferential force is greater during rotation of the nut 106 that detaches the nut 106 from the distal connector 32 than during rotation of the nut that attaches the nut 106 to the distal connector 32.

The angle of contact between the protrusions 118 and the notches 125 can contribute to the differential resistance. In one direction of rotation of the nut 106, for example, when affixing the nut 106 to the distal connector 32, the contact angle between the protrusions 118 and the notches 125 allows the protrusions 118 to slide out of the notches 125 relatively easily. When attaching the nut 106, the force on the elements 116 is compressive as the protrusions 118 engage the notches 125. Compression bends the elements 116 slightly, changing the angle of contact between the protrusions 118 and the notches 125 and assisting the protrusions 118 to slide out of the notches 125.

In the opposite direction of rotation of the nut 106, when detaching the nut 106 from the distal connector 32, the contact angle between the protrusions 118 and the notches 125 requires additional force to complete the rotation. When detaching the nut 106 (for example, during counter-clockwise rotation from the view in FIG. 5C), the force on the elements 116 is tensile. The tensile force causes the elements 116 to become straighter, which changes the contact angle of the protrusions with the notches 125 and increases the force required to complete rotation of the nut 106. The straightening of the elements 116 increases the force between the protrusions 118 and the notches 125, which translates into greater circumferential force that resists rotation of the nut 106.

Because the resistance to detach the nut 106 is greater than the resistance to attach the nut 106, the asymmetric resistance discourages accidental detachment of the in-line connector 28 from the distal connector 32 so that the electrical connection between the pump controller and the pump 12 is not accidentally broken.

Referring to FIG. 7A, the distal connector 32 of the percutaneous portion 18 includes a housing 138, a cap 131, and a bend relief 132. The housing 138 includes an exterior threaded portion 128 that engages the threaded inner surface 120 of the nut 106 to secure the in-line connector 28 to the distal connector 32. Near the threaded portion 128, the housing 138 includes a warning stripe 130, which can be colored, that indicates when the nut 106 is at least partially disengaged from the housing 138. When the nut 106 is fully engaged, the nut 106 covers the warning stripe 130. As the nut 106 disengages from the housing 138, the nut 106 travels relative to the housing 138 and uncovers the warning stripe 130 to indicate that the nut 106 is not fully engaged.

The cap 131 and the bend relief 132 form an assembly 133 that is placed over the percutaneous cable 34 and couples to the housing 138. To create the assembly 133, the bend relief 132 is formed, for example, by molding polyurethane around a metal core and a portion of the cap 131. The bend relief 132 includes a smooth exterior to facilitate tunneling of the distal connector 32 through a body cavity of a patient. The bend relief 132 and the cap 131 are removed from the metal core as the assembly 133, and the assembly 133 is placed over the percutaneous cable 34. The bend relief 132 is adhesively bonded to the silicone outer jacket 52 of the percutaneous cable 34.

Figure 7C:
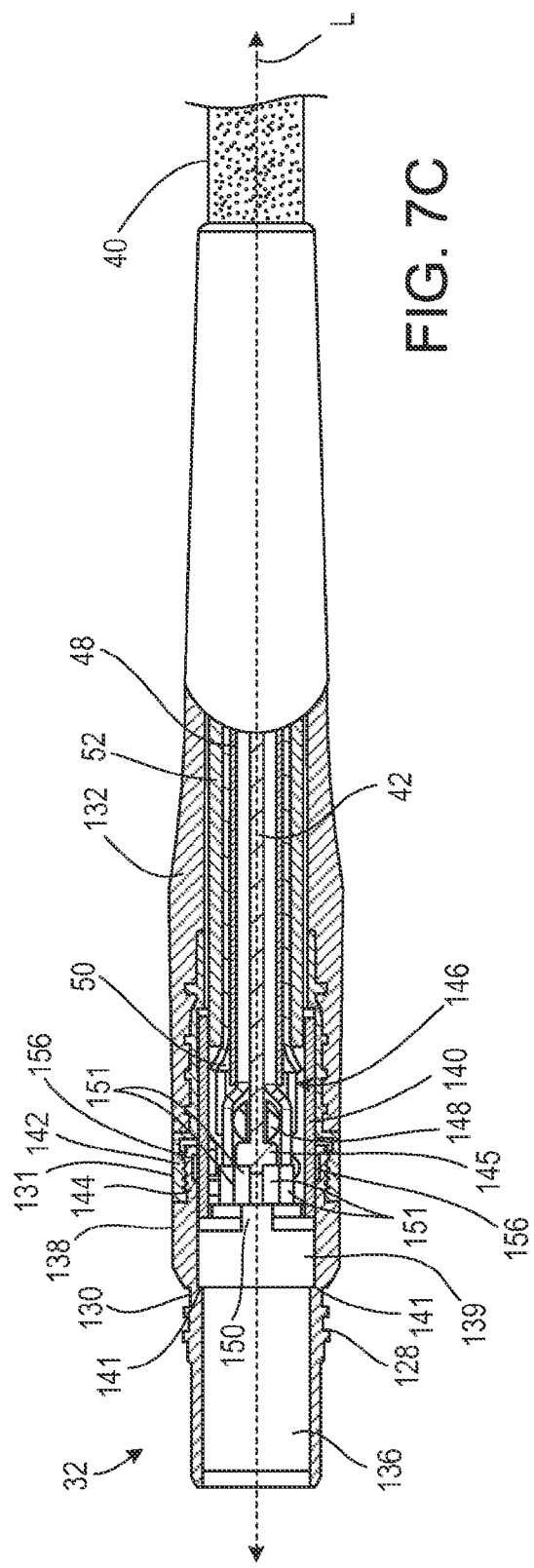
FIG. 7C is a side cutaway view of the distal connector of the percutaneous portion.
Figure 7D:
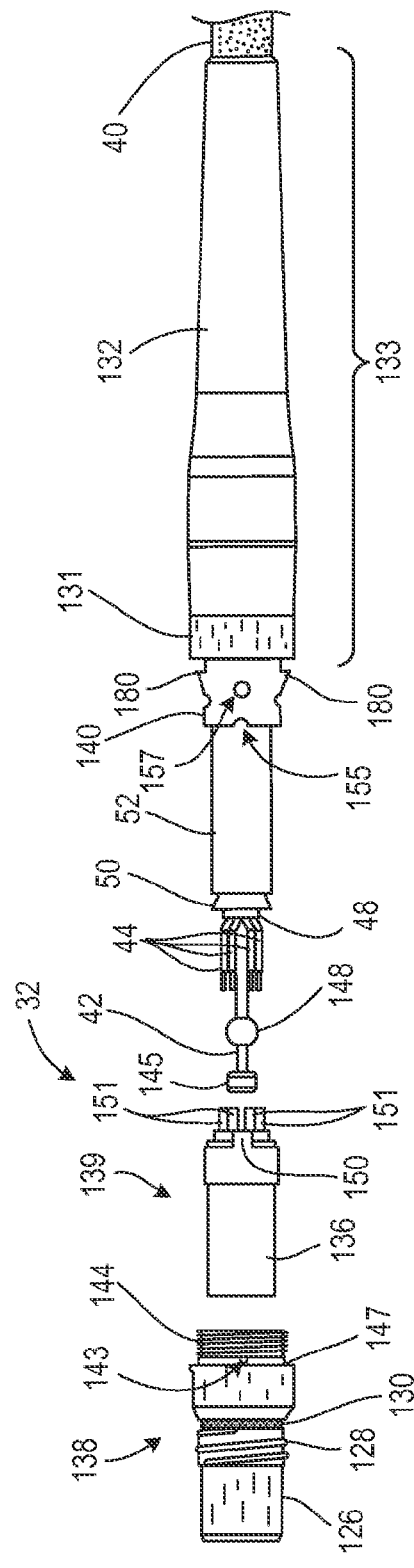
FIG. 7D is an exploded view of the distal connector of the percutaneous portion.
Figure 7E:
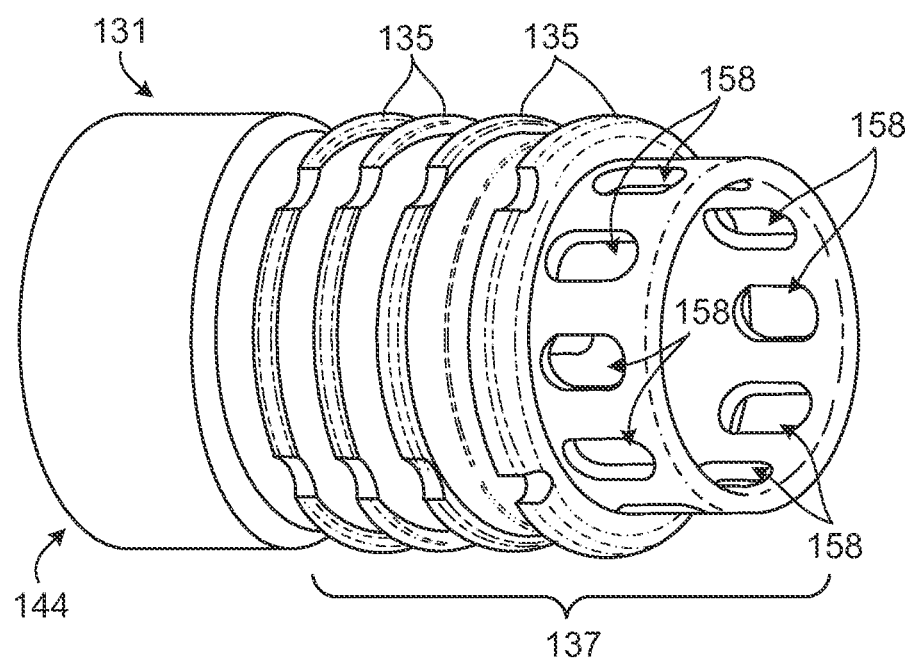
FIG. 7E is a perspective view of a cap of the distal connector of FIG. 7A.

FIG. 7E illustrates the cap 131 in greater detail. The portion 137 of the cap 131 over which the bend relief 132 is molded includes circumferential ridges 135 that secure the bend relief 132 to the cap 131. The cap 131 defines holes 159 that admit material during the process of molding the bend relief 132.

Referring to FIG. 7B, the housing 138 includes a tubular end 126 that is configured to engage the in-line connector 28. Located within the tubular end 126 of the housing 138, the distal connector 32 includes a socket 134 and an alignment rim 136. When the distal connector 32 couples to the in-line connector 28, the tubular end 126 is received in the housing 100 of the in-line connector 28. After the electrical connection is made, the tubular end 126 of the housing 138 engages the o-rings 107 of the in-line connector 28 to seal the interface between the distal connector 32 and the in-line connector 28.

The distal connector 32 also defines an alignment slot 129 that receives the alignment rim 94 of the in-line connector. Additionally, when the in-line connector 28 is misaligned with the distal connector 32, the alignment rim 136 of the distal connector 32 engages the alignment rim 94 of the in-line connector 28 to prevent engagement at an incorrect radial alignment. When the correct radial alignment is achieved, the alignment slot 129 receives the alignment rim 94 of the in-line connector 28.

When the in-line connector 28 and the distal connector 32 are connected, the pins 92 of the in-line connector 28 are received in the socket 134 of the distal connector 32, establishing electrical connections between the modular portion 16 and the percutaneous portion 18. The electrical connections are established as soon as the pins 92 enter the socket 134, even before the nut 106 of the in-line connector 28 engages the threaded portion 128 of the distal connector 32 to fully secure the in-line connector 28 to the distal connector 32.

Referring to FIGS. 7C and 7D, the assembly 133 couples to the housing 138 to cover the terminations of the percutaneous cable 34. The housing 138 includes an outer threaded region 144 and the cap 131 of the assembly 133 includes an inner threaded region 142. Engagement of the threaded regions 142 and 144 secures the housing 138 to the assembly 133. The cap 131 and the housing 138 can also be secured by a thread-locking adhesive or a weld.

The distal connector 32 includes a connector body 139 and a spacer 140 located between the cap 131 and the housing 138. The connector body 139 includes the socket 134 and is coupled to the alignment rim 136. The connector body 139 includes contacts 151 to receive the conductors 44 of the percutaneous cable 34. The connector body 139 is positioned between the engagement surface 141 of the housing 138 and the spacer 140.

Figure 7F:
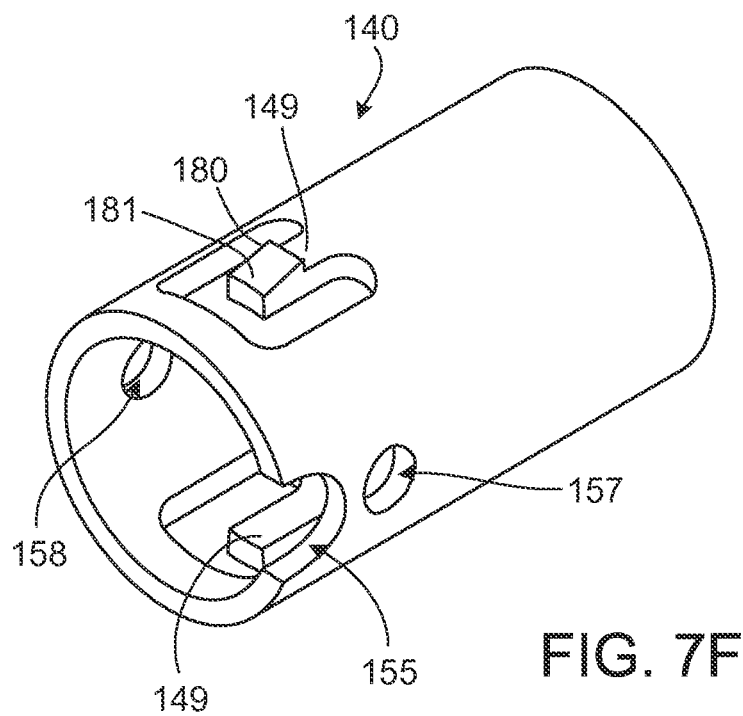
FIG. 7F is a perspective view of a spacer of the distal connector of FIG. 7A.

Referring to FIG. 7F, the spacer 140 is generally formed in the shape of a hollow cylinder. The spacer 140 also includes two tabs 149 integral to the spacer 140, located opposite each other around the circumference of the spacer 140. The spacer 140 also defines a notch 155 at one end that can receive an uneven feature of the connector body 139, such as a key 150. Each tab 149 forms a stop 180 with an angled portion 181 extending out from the spacer 140 that secures the spacer 140 to the housing 138.

Referring again to FIGS. 7C and 7D, the connector body 139 is captured between the spacer 140 and the housing 138. The housing 138 includes a circumferential engagement surface 141 that limits travel of elements within the housing 138. The housing 138 also defines a circumferential groove 156 that receives the two tabs 149 of the spacer 140. To assemble the distal connector 32, the connector body 139 enters the housing 138 and abuts the engagement surface 141 of the housing 138. The spacer 140 then attaches to the housing 138 to capture the connector body 139 in the housing 138. As the spacer 140 enters the housing 138, the angled portion 181 of the stops 180 contacts the interior of the housing 138 and deflects the tabs 149 inward. The spacer 140 continues to advance until the stops 180 of the tabs 149 enter the circumferential groove 156 on the interior of the housing 138. The tabs 149 straighten and the engagement of the stops 180 in the circumferential groove 156 limits axial movement of the spacer 140 relative to the housing 138, capturing the connector body 139 within the housing 138.

The spacer 140, the connector body 139, and the percutaneous cable 34 define a solder pocket 146 (e.g., a chamber) in which the elements of the percutaneous cable 34 are terminated. The cable core 41, armor braid 50, and outer jacket 52 all enter the solder pocket 146 straight along the longitudinal axis, L. This orientation enables the percutaneous cable 34 to be terminated in the distal connector 32 with a small outer diameter. The small outer diameter permits the distal connector 32 to be tunneled through a body cavity and through a small exit site. The inner strength member 42 terminates at an end 145 that passes through a retention ball 148 and is knotted to prevent the end 145 of the inner strength member 42 from slipping. The conductors 44 bend around the retention ball 148 and are attached to the connector body 139 to electrically connect with the socket 134. The retention ball 148 has a generally spherical shape and defines a hole to admit the inner strength member 42. Alternatively, the inner strength member 42 can be secured using no knots or multiple knots. Instead of a retention ball 148, a retaining member of another shape can be used. The armor braid 50 flares outward from the cable core 41 in the solder pocket 146 to receive potting material between the armor braid 50 and the extruded layer 48 to secure the armor braid 50 in the solder pocket 146.

Referring to FIG. 7D, to anchor the terminations of the percutaneous cable 34, a potting material of, for example, high-strength epoxy is introduced into the solder pocket 146. The housing 138 defines a hole 143 at a circumferential thread relief 147 adjacent the outer threaded region 144. When the spacer 140 engages the housing 138, the hole 143 defined through the housing 138 is aligned over a hole 157 defined through the spacer 140. A syringe or other instrument can be inserted through the holes 143, 157 to introduce potting material into the solder pocket 146. Potting flows proximally within the spacer 140, filling the solder pocket 146 and gaps between the inner surface of the spacer 140 and the outer jacket 52 of the percutaneous cable 34.

Referring to FIG. 7F, the spacer 140 defines at least one hole 158 that allows potting to flow through the spacer 140 and bond to the housing 138. The hole 158 is placed so that potting can enter the circumferential groove 156 of the housing 138, in which the stops 180 of the tabs 149 reside.

Figure 7G:
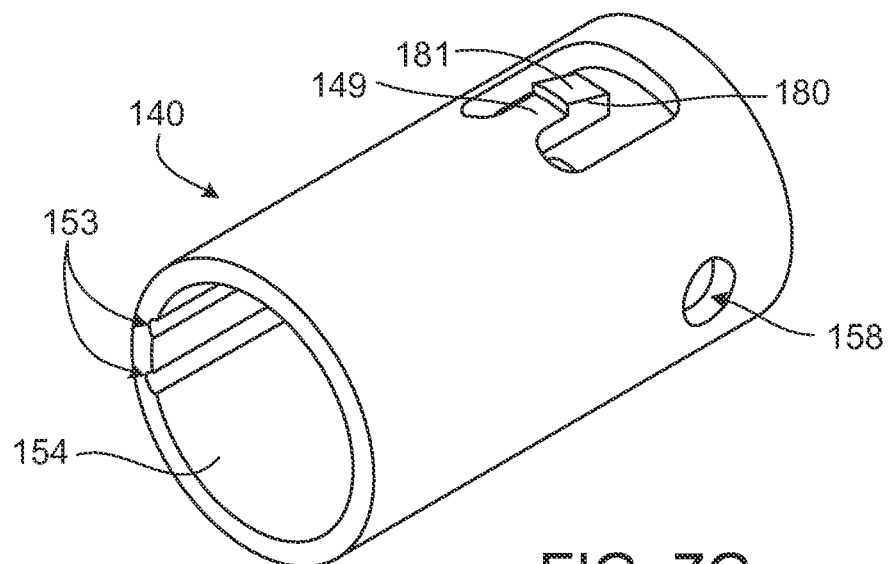
FIG. 7G is another perspective view of the spacer of the distal connector of FIG. 7A.

Referring to FIG. 7G, the spacer 140 also defines longitudinal grooves 153 located partially along an inner surface 154 of the spacer 140. The longitudinal grooves 153 permit air to vent from the solder pocket 146 as the potting is introduced.

The potting material is cured by ultraviolet light, and when hardened, secures the conductors 44, the end 145 of the inner strength member 42, the flared end of the armor braid 50, and other terminations of the percutaneous cable 34. The hardened epoxy resists becoming dislodged or deformed when axial loads are exerted on the percutaneous cable 34. After potting material has been cured, the assembly 133, which includes the cap 131 and the bend relief 132, is secured to the housing 138 by a threaded connection, as described above.

Figure 8C:
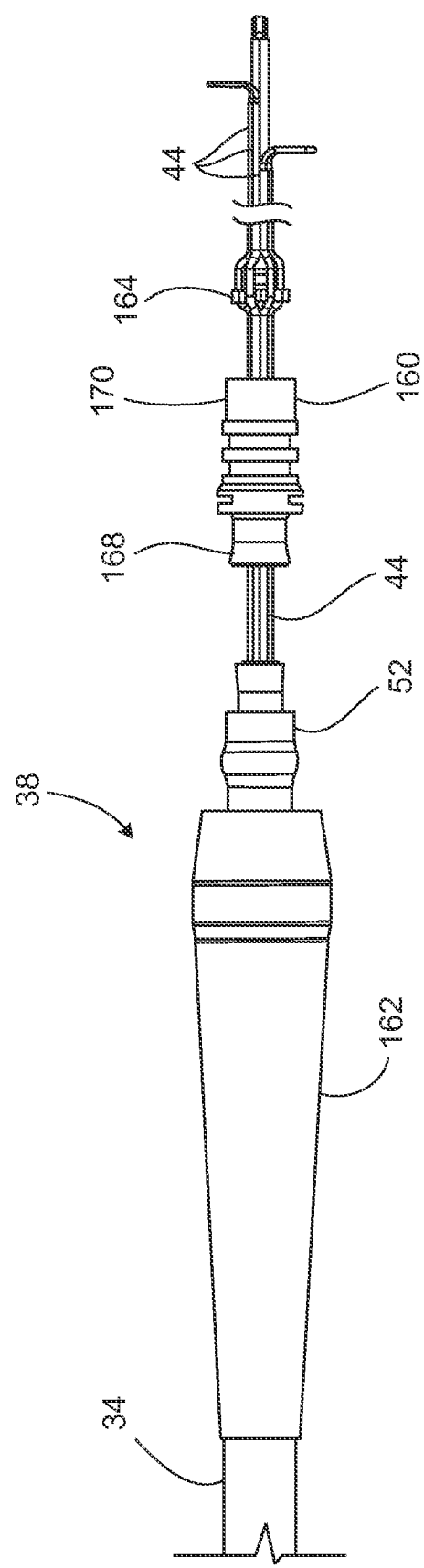
FIG. 8C is an exploded view of the proximal end of the percutaneous portion.

Referring to FIGS. 8A, 8B, and 8C, the proximal connector 38 of the percutaneous portion 18 includes a support structure 160 within a bend relief 162. The bend relief 162 is formed, for example, by molding silicone around a core. The bend relief 162 is then placed over the percutaneous cable 34 and bonded to the outer jacket 52 of the percutaneous cable 34 with an adhesive. The conductors 44 of the percutaneous cable 34 connect to the pump 12 after passing through the support structure 160 and bending around a retention clip 164. The inner strength member 42 passes through the retention clip 164 and is knotted to prevent the inner strength member 42 from slipping through the retention clip 164. The retention clip 164 is disposed within the support structure 160 and abuts an internal wall 169 of the support structure 160.

The support structure 160 includes an end 170 and a flared end 168. The end 170 is received by the pump 12. The flared end 168 of the support structure 160 is inserted under the outer jacket 52 of the percutaneous cable 34 and is adhesively bonded to the outer jacket 52. The outer jacket 52 is deformed to conform to the shape of the support structure 160. In an alternative implementation, the support structure 160 is disposed about the exterior of the outer jacket 52 and is not inserted under the outer jacket 52.

Referring to FIG. 8B, the interior of the support structure 160 can define a solder pocket 166 (e.g., a chamber) that secures the components of the percutaneous cable 34. The components of the percutaneous cable 34 enter the solder pocket 166 in a straight orientation along the longitudinal axis, L, of the proximal connector 36. A potting material of, for example, high-strength epoxy is introduced into the solder pocket 166, and the potting material is cured by ultraviolet light.

Figure 9A:
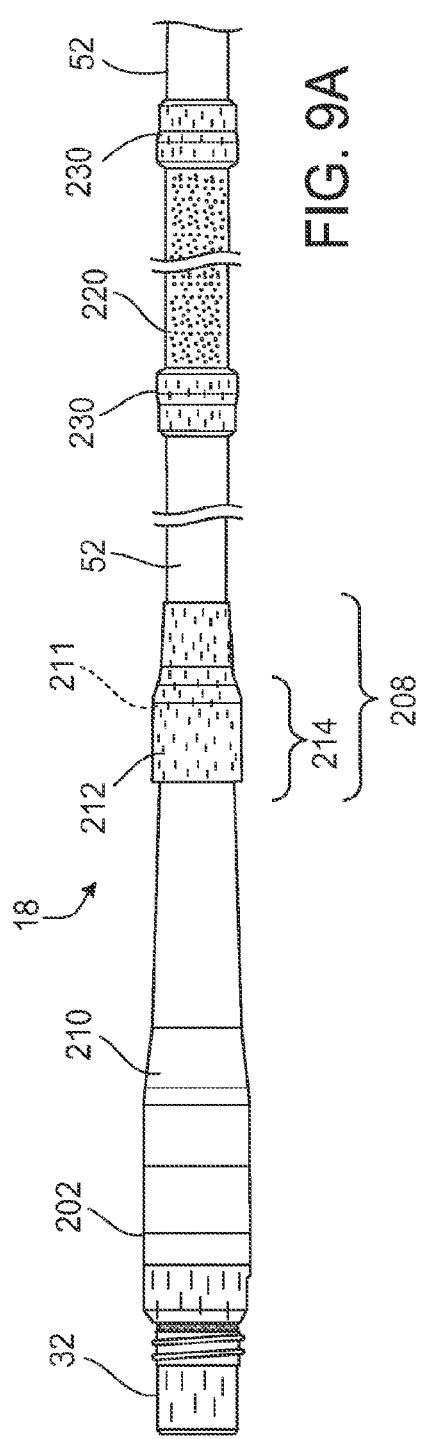
FIG. 9A is an illustration of an alternative percutaneous portion of the driveline.

Referring to FIG. 9A, an alternative percutaneous portion 200 for the cable 14 includes a distal connector 202 located at a distal end 204, a percutaneous cable 206, and a pump-end connector (not shown) at a proximal end, each being formed as described above for the percutaneous portion 18. The percutaneous cable 206 includes an outer jacket 52 formed of, for example, silicone, and the distal connector 202 includes a bend relief 210 that is formed, for example, of polyurethane and adhered to the outer jacket 52.

The percutaneous portion 200 has a velour outer portion 220 that is spaced apart from the distal connector 202 along the percutaneous cable 206 rather than adjacent to the bend relief 210. To attach the velour outer portion 220, a sheet of velour material can be formed into a tube about the silicone outer jacket 52. An adhesive applied to the outer jacket 52 captures portions of the velour material to the outer jacket 52 holding the velour outer portion 220 in place. To reduce fraying and other wear of the velour outer portion 220, covers 230 formed of, for example, silicone, are molded over the ends of the velour outer portion 220.

Surrounding the percutaneous portion 200 at a transition region between an end 211 of the bend relief 210 and the outer jacket 52 is a cover 212 that seals over the region at which the outer diameter of the percutaneous portion 200 changes. The cover 212 limits debris from entering between the outer jacket 52 and the bend relief 210, which reduces the collection of potentially infectious agents near an exit site of the percutaneous portion 200 from a patient's body. The cover 212 also provides strain relief, protecting the percutaneous cable 206 against forces localized at the end 211 of the bend relief 210.

The cover 212 is formed by overmolding a material such as silicone onto the percutaneous cable 206 and an end region 214 of the bend relief 210. Because silicone does not easily bond to polyurethane, an end region the polyurethane bend relief 210 is pre-treated to chemically activate the bend relief and make it more receptive to bonding. For example, the end region 214 can be exposed to a plasma to activate the polyurethane. A primer or silicone layer may be applied to the activated region to form an outer layer of silicone fused with the polyurethane. Silicone is then molded over the activated end region 214 and over a portion of the silicone outer jacket 52. In some implementations, a room-temperature vulcanizing (RTV) silicone forms the cover 212.

Figure 9B:
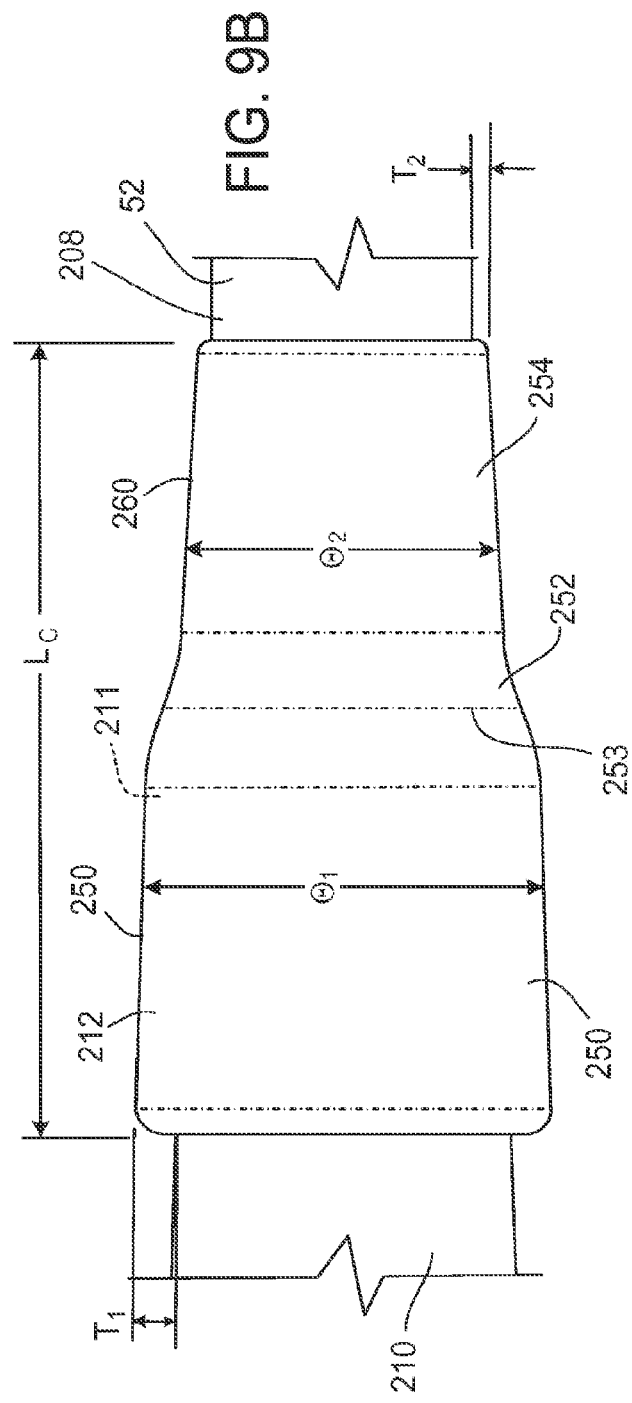
FIG. 9B is an illustration of a cover of the percutaneous portion of FIG. 9A.

Referring to FIG. 9B, the cover 212 includes a distal end region 250, a central region 252, and a proximal end region 254. Thicknesses, $T_1$, $T_2$, of the cover 212 at the end regions 252, 254 are, for example, approximately 0.005 inches to 0.030 inches, or between approximately 0.010 to 0.015 inches. Included taper angles, $\Theta_1$, $\Theta_2$, at the exterior of the end regions 252, 254 are, for example, between approximately 0 degrees and 10 degrees, or between approximately 2 degrees and 8 degrees. In some implementations, the taper angles, $\Theta_1$, $\Theta_2$, are 4 degrees and 6 degrees respectively. In some implementations, a length, $L_C$, of the cover 212 is, for example, between approximately 0.5 inches and 1.5 inches, or between approximately 0.6 and 0.9 inches.

In the illustrated implementation, over the central region 250, the outer diameter of the cover 212 decreases with a steeper transition than the taper angles $\Theta_1$, $\Theta_2$. To limit the amount of stress occurring at the end 211, a center 253 of the central region 250 is offset from the end 211 of the bend relief 210, for example, spaced proximally from the end 211 by between approximately 0 and 0.25 inches, or between approximately 0.06 and 0.018 inches.

A number of implementations have been described. Nevertheless, it will be understood that various modifications may be made without departing from the spirit and scope of the disclosure. Accordingly, other implementations are within the scope of the following claims.

What is claimed is:

1. A method of implanting a blood pump, the method comprising:
    implanting the blood pump within a patient;
    connecting a proximal end of a percutaneous cable portion to the blood pump;
    connecting a proximal end of a modular cable portion to a distal end of the percutaneous cable portion;
    securing the proximal end of the modular cable portion to the distal end of the percutaneous cable portion so as to prevent axial separation between the modular cable portion and the percutaneous cable portion; and
    wherein the percutaneous cable portion and the modular cable portion connect to form a blood pump driveline;
    wherein the connection of the proximal end of the modular cable portion to the distal end of the percutaneous cable portion is external to the patient.

2. The method of claim 1, further comprising connecting a distal end of the modular cable portion to a blood pump controller.

3. The method of claim 1, further comprising implanting a majority of the percutaneous cable portion within the patient while at least the distal end of the percutaneous cable portion remains external to the patient, and wherein the modular cable portion remains external to the patient.

4. The method of claim 1,
wherein connecting the proximal end of the modular cable portion to the distal end of the percutaneous cable portion comprises axially translating the proximal end of the modular cable portion relative to the distal end of the percutaneous cable portion to electrically connect the modular cable portion and the percutaneous cable portion; and
wherein securing comprises engaging an engagement feature to axially secure the proximal end of the modular cable portion to the distal end of the percutaneous cable portion after electrically connecting the modular cable portion and the percutaneous cable portion.

5. The method of claim 4, wherein the engagement feature comprises a threaded engagement feature.

6. The method of claim 5, wherein the threaded engagement feature is non-threadedly, rotatably, and axially moveable relative to the modular cable portion or the percutaneous cable portion when disengaged.

7. The method of claim 5, wherein the threaded engagement feature comprises a rotatable nut, and wherein the rotatable nut provides a first resistance against rotation in a first direction and a second resistance against rotation in a second direction opposite the first direction.

8. The method of claim 7, wherein the first direction is an engagement direction for securing the modular cable portion and the percutaneous cable portion and the second direction is a disengagement direction for disengaging the modular cable portion and the percutaneous cable portion and wherein the first resistance is less than the second resistance.

9. The method of claim 7, wherein the rotatable nut comprises a protrusion that protrudes inwardly from the nut, and wherein the protrusion engages with ridges and notches formed on an outer surface of the modular cable portion or the percutaneous portion to provide the first resistance and the second resistance when rotating the nut in the first direction and the second direction.

10. The method of claim 1, wherein connecting the proximal end of the modular cable portion to the distal end of the percutaneous cable portion comprises inserting pins of the modular cable portion into corresponding sockets of the percutaneous cable portion.

11. The method of claim 1, wherein a distal end of the modular cable is configured to directly couple with a blood pump controller.

12. A method of implanting a blood pump, the method comprising:
implanting the blood pump within a patient;
connecting a proximal end of a percutaneous cable portion to the blood pump;
connecting a proximal end of a modular cable portion to a distal end of the percutaneous cable portion;
securing the proximal end of the modular cable portion to the distal end of the percutaneous cable portion so as to prevent axial separation between the modular cable portion and the percutaneous cable portion; and
wherein the percutaneous cable portion and the modular cable portion connect to form a blood pump driveline;
wherein connecting the proximal end of the modular cable portion to the distal end of the percutaneous cable portion comprises axially translating the proximal end of the modular cable portion relative to the distal end of the percutaneous cable portion to electrically connect the modular cable portion and the percutaneous cable portion; and
wherein securing comprises engaging an engagement feature to axially secure the proximal end of the modular cable portion to the distal end of the percutaneous cable portion after electrically connecting the modular cable portion and the percutaneous cable portion;
wherein engaging the engagement feature comprises covering an indicator with the engagement feature until the indicator is no longer visible, the indicator, when visible, indicating when the engagement feature is at least partially disengaged with the engagement feature.

13. A method of replacing a modular portion of a heart pump driveline, the driveline having a percutaneous portion with a proximal end and a distal end opposite the proximal end, the proximal end of the percutaneous portion coupled with an implanted heart pump and the distal end of the percutaneous portion coupled with a proximal end of the modular portion, the method comprising:
disconnecting the proximal end of the modular portion from the distal end of the percutaneous portion;
connecting a proximal end of a replacement modular portion to the distal end of the percutaneous portion;
wherein the connection of the proximal end of the replacement modular portion to the distal end of the percutaneous cable portion is external to the patient.

14. The method of claim 13, further comprising connecting a distal end of the replacement modular portion to a heart pump controller.

15. The method of claim 13, further comprising disconnecting a distal end of the modular portion from a heart pump controller.

16. The method of claim 13, wherein disconnecting the proximal end of the modular portion from the distal end of the percutaneous portion comprises disengaging an engagement feature axially securing the proximal end of the modular portion with the distal end of the percutaneous portion.

17. The method of claim 16, wherein disengaging the engagement feature axially securing the proximal end of the modular portion with the distal end of the percutaneous portion does not axially translate the modular portion relative to the percutaneous portion.

18. The method of claim 13, wherein connecting the proximal end of the replacement modular portion to the distal end of the percutaneous portion comprises axially translating the proximal end of the modular portion relative to the distal end of the percutaneous portion to electrically connect the replacement modular portion with the percutaneous portion.

19. The method of claim 18, further comprising, after electrically connecting the replacement modular portion with the percutaneous portion, engaging an engagement feature to secure the proximal end of the modular portion with the distal end of the percutaneous portion.

20. The method of claim 19, wherein the engagement feature comprises a threaded engagement feature.

21. The method of claim 13, wherein a distal end of the replacement modular portion is configured to directly couple with a blood pump controller.

22. A method of replacing a modular portion of a heart pump driveline, the driveline having a percutaneous portion with a proximal end and a distal end opposite the proximal end, the proximal end of the percutaneous portion coupled with an implanted heart pump and the distal end of the percutaneous portion coupled with a proximal end of the modular portion, the method comprising:
disconnecting the proximal end of the modular portion from the distal end of the percutaneous portion;
connecting a proximal end of a replacement modular portion to the distal end of the percutaneous portion;

wherein disconnecting the proximal end of the modular portion from the distal end of the percutaneous portion comprises disengaging an engagement feature axially securing the proximal end of the modular portion with the distal end of the percutaneous portion;

wherein disengaging the engagement feature axially securing the proximal end of the modular portion with the distal end of the percutaneous portion does not interrupt an electrical connection between the modular portion and the percutaneous portion.

23. The method of claim 22, further comprising, after disengaging the engagement feature, axially separating the proximal end of the modular portion from the distal end of the percutaneous portion to electrically disconnect the modular portion from the percutaneous portion.

24. A method of replacing a modular portion of a heart pump driveline, the driveline having a percutaneous portion with a proximal end and a distal end opposite the proximal end, the proximal end of the percutaneous portion coupled with an implanted heart pump and the distal end of the percutaneous portion coupled with a proximal end of the modular portion, the method comprising:
   disconnecting the proximal end of the modular portion from the distal end of the percutaneous portion;
   connecting a proximal end of a replacement modular portion to the distal end of the percutaneous portion;
   wherein connecting the proximal end of the replacement modular portion to the distal end of the percutaneous portion comprises axially translating the proximal end of the modular portion relative to the distal end of the percutaneous portion to electrically connect the replacement modular portion with the percutaneous portion;
   further comprising, after electrically connecting the replacement modular portion with the percutaneous portion, engaging an engagement feature to secure the proximal end of the modular portion with the distal end of the percutaneous portion; and
   wherein engaging the engagement feature to secure the proximal end of the modular portion with the distal end of the percutaneous portion covers an indicator that indicates when the engagement feature is at least partially disengaged.

25. The method of claim 24, wherein engaging the engagement feature comprises engaging the engagement feature until the indicator is no longer visible.

26. A method of connecting a blood pump implanted within a patient to a blood pump controller, the blood pump coupled with a percutaneous cable portion, and wherein a distal end of the percutaneous cable portion extends externally from the patient, the method comprising:
   connecting a proximal end of a modular cable portion to the distal end of the percutaneous cable portion, the percutaneous cable portion and the modular cable portion connecting to form a blood pump driveline;
   securing the proximal end of the modular cable portion to the distal end of the percutaneous cable portion so as to prevent axial separation between the modular cable portion and the percutaneous cable portion; and
   connecting a distal end of the modular cable portion to the blood pump controller;
   wherein the connection of the proximal end of the modular cable portion to the distal end of the percutaneous cable portion is external to the patient.

27. The method of claim 26,
   wherein connecting the proximal end of the modular cable portion to the distal end of the percutaneous cable portion comprises axially translating the proximal end of the modular cable portion relative to the distal end of the percutaneous cable portion to electrically connect the modular cable portion and the percutaneous cable portion; and
   wherein securing comprises engaging an engagement feature to axially secure the proximal end of the modular cable portion to the distal end of the percutaneous cable portion after electrically connecting the modular cable portion and the percutaneous cable portion.

28. The method of claim 27, wherein the engagement feature comprises a threaded engagement feature.

29. The method of claim 28, wherein the threaded engagement feature is non-threadedly, rotatably, and axially moveable relative to the modular cable portion or the percutaneous cable portion when disengaged.

30. The method of claim 28, wherein the threaded engagement feature comprises a rotatable nut, and wherein the rotatable nut provides a first resistance against rotation in a first direction and a second resistance against rotation in a second direction opposite the first direction.

31. The method of claim 30, wherein the first direction is an engagement direction for securing the modular cable portion and the percutaneous cable portion and the second direction is a disengagement direction for disengaging the modular cable portion and the percutaneous cable portion and wherein the first resistance is less than the second resistance.

32. The method of claim 30, wherein the rotatable nut comprises a protrusion that protrudes inwardly from the nut, and wherein the protrusion engages with ridges and notches formed on an outer surface of the modular cable portion or the percutaneous portion to provide the first resistance and the second resistance when rotating the nut in the first direction and the second direction.

33. The method of claim 26, wherein connecting the proximal end of the modular cable portion to the distal end of the percutaneous cable portion comprises inserting pins of the modular cable portion into corresponding sockets of the percutaneous cable portion.

34. The method of claim 26, wherein the distal end of the modular cable portion is configured to directly couple with the blood pump controller.

35. A method of connecting a blood pump implanted within a patient to a blood pump controller, the blood pump coupled with a percutaneous cable portion, and wherein a distal end of the percutaneous cable portion extends externally from the patient, the method comprising:
   connecting a proximal end of a modular cable portion to the distal end of the percutaneous cable portion, the percutaneous cable portion and the modular cable portion connecting to form a blood pump driveline;
   securing the proximal end of the modular cable portion to the distal end of the percutaneous cable portion so as to prevent axial separation between the modular cable portion and the percutaneous cable portion; and
   connecting a distal end of the modular cable portion to the blood pump controller
   wherein connecting the proximal end of the modular cable portion to the distal end of the percutaneous cable portion comprises axially translating the proximal end of the modular cable portion relative to the distal end of the percutaneous cable portion to electrically connect the modular cable portion and the percutaneous cable portion; and
   wherein securing comprises engaging an engagement feature to axially secure the proximal end of the modular cable portion to the distal end of the percutaneous cable portion after electrically connecting the modular cable portion and the percutaneous cable portion; and wherein engaging the engagement feature comprises covering an indicator with the engagement feature until the indicator is no longer visible, the indicator, when visible, indicating when the engagement feature is at least partially disengaged with the engagement feature.

* * * * *